US009932326B2

(12) United States Patent
Coats et al.

(10) Patent No.: US 9,932,326 B2
(45) Date of Patent: *Apr. 3, 2018

(54) POTENT AND SELECTIVE INHIBITORS OF HEPATITIS C VIRUS

(71) Applicants: Cocrystal Pharma, LLC, Tucker, GA (US); Emory University, Atlanta, GA (US)

(72) Inventors: Steven J. Coats, McDonough, GA (US); Franck Amblard, Tucker, GA (US); Hongwang Zhang, Tucker, GA (US); Longhu Zhou, Atlanta, GA (US); Richard Anthony Whitaker, Loganville, GA (US); Tamara Rosario McBrayer, Atlanta, GA (US); Raymond F. Schinazi, Miami, FL (US); Junxing Shi, Duluth, GA (US)

(73) Assignees: Cocrystal Pharma, LLC, Tucker, GA (US); Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/936,878

(22) Filed: Nov. 10, 2015

(65) Prior Publication Data

US 2016/0068518 A1 Mar. 10, 2016

Related U.S. Application Data

(63) Continuation of application No. 14/455,197, filed on Aug. 8, 2014, now Pat. No. 9,181,227, which is a continuation of application No. 13/817,522, filed as application No. PCT/US2011/049426 on Aug. 26, 2011, now Pat. No. 8,859,595.

(60) Provisional application No. 61/377,452, filed on Aug. 26, 2010, provisional application No. 61/494,877, filed on Jun. 8, 2011.

(51) Int. Cl.
A61K 31/4178 (2006.01)
C07D 403/14 (2006.01)
C07D 403/04 (2006.01)
C07D 405/14 (2006.01)
C07D 413/14 (2006.01)
A61K 31/4192 (2006.01)
A61K 31/444 (2006.01)
A61K 31/506 (2006.01)
A61K 31/5377 (2006.01)
A61K 31/655 (2006.01)
C07D 401/14 (2006.01)
C07D 407/14 (2006.01)
A61K 45/06 (2006.01)

(52) U.S. Cl.
CPC ........ C07D 403/14 (2013.01); A61K 31/4178 (2013.01); A61K 31/4192 (2013.01); A61K 31/444 (2013.01); A61K 31/506 (2013.01); A61K 31/5377 (2013.01); A61K 31/655 (2013.01); A61K 45/06 (2013.01); C07D 401/14 (2013.01); C07D 403/04 (2013.01); C07D 405/14 (2013.01); C07D 407/14 (2013.01); C07D 413/14 (2013.01)

(58) Field of Classification Search
None
See application file for complete search history.

(56) References Cited

U.S. PATENT DOCUMENTS

| 8,329,159 | B2* | 12/2012 | Belema ............... C07D 401/14 424/85.2 |
| 2008/0050336 | A1* | 2/2008 | Bachand ............. C07D 401/14 424/85.2 |
| 2008/0311075 | A1 | 12/2008 | Bachand et al. |
| 2009/0068140 | A1 | 3/2009 | Bachand et al. |
| 2009/0202478 | A1 | 8/2009 | Bachand et al. |
| 2010/0158862 | A1 | 6/2010 | Kim et al. |
| 2010/0310512 | A1 | 12/2010 | Guo et al. |

FOREIGN PATENT DOCUMENTS

| WO | 2004014313 A2 | 2/2004 |
| WO | 2004014852 A2 | 2/2004 |
| WO | 2006133326 A1 | 12/2006 |
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |

(Continued)

OTHER PUBLICATIONS

Conte, I., et al., "Synthesis and SAR of piperazinyl-N-phenylbenzamides as inhibitors of hepatitis C virus RNA replication in cell culture", "Bioorganic & Medicinal Chemistry Letters", Jan. 27, 2009, pp. 1779-1783, vol. 19.

Dousson, C., "Building a Leading Antiviral Franchise: Next generation HCV NS5A inhibitor: In vitro antiviral optimization for pan-genotypic activity and preclinical profile", "Presentation at 26th International Conference on Antiviral Research, San Francisco, CA", May 12, 2013, Publisher: Idenix Pharmaceuticals.

Fridell, R., et al., "Distinct Functions of NS5A in HCV RNA Replication Uncovered by Studies with the NS5A Inhibitor BMS-790052", "J. Virol.", May 18, 2011, pp. 7312-7320, vol. 85, No. 14.

Gao, M., et al., "Chemical genetics strategy identifies an HCV NS5A inhibitor with a potent clinical effect", "Nature", Apr. 21, 2010, pp. 96-100, vol. 465, No. 7294.

Hamatake, R., et al., "Chapter 22: HCV Inhibition Mediated Through the Nonstructural Protein 5A (NS5A) Replication Complex", "Annual Reports in Medicinal Chemistry", Oct. 8, 2012, pp. 331-345, vol. 47.

Romine, J., et al., "Inhibitors of HCV NS5A: From Iminothiazolidinones to Symmetrical Stilbenes", "ACS Med. Chem. Lett.", Jan. 11, 2011, pp. 224-229, vol. 2.

(Continued)

Primary Examiner — Samantha Shterengarts
(74) Attorney, Agent, or Firm — David Bradin; Andrews Kurth Kenyon LLP

(57) ABSTRACT

The present invention is directed to compounds, compositions and methods for treating or preventing hepatitis C virus (HCV) infection in human subjects or other animal hosts. The compounds are as also pharmaceutically acceptable, salts, prodrugs, and other derivatives thereof as pharmaceutical compositions and methods for treatment or prevention of HCV infection.

10 Claims, 1 Drawing Sheet

(56) References Cited

FOREIGN PATENT DOCUMENTS

| | | |
|---|---|---|
| WO | 2009102325 A1 | 8/2009 |
| WO | 2009102568 A1 | 8/2009 |
| WO | 2009102633 A1 | 8/2009 |
| WO | 2010017401 A1 | 2/2010 |
| WO | 2010027564 A2 | 3/2010 |
| WO | 2010030592 A1 | 3/2010 |
| WO | 2010039793 A1 | 4/2010 |
| WO | 2010065668 A1 | 6/2010 |
| WO | 2010096302 A1 | 8/2010 |
| WO | 2010111483 A1 | 9/2010 |
| WO | 2011075439 A1 | 6/2011 |
| WO | 2011075615 A1 | 6/2011 |
| WO | 2011082077 A1 | 7/2011 |
| WO | 2011112429 A1 | 9/2011 |
| WO | 2012003642 A1 | 1/2012 |
| WO | 2012018325 A1 | 2/2012 |
| WO | 2012018534 A1 | 2/2012 |
| WO | 2012018829 A1 | 2/2012 |
| WO | 2012021591 A1 | 2/2012 |
| WO | 2012039717 A1 | 3/2012 |
| WO | 2012040923 A1 | 4/2012 |
| WO | 2012040924 A1 | 4/2012 |
| WO | 2012041014 A1 | 4/2012 |
| WO | 2012041227 A1 | 4/2012 |
| WO | 2012050848 A1 | 4/2012 |
| WO | 2012050850 A1 | 4/2012 |
| WO | 2012135581 A1 | 10/2012 |
| WO | 2012166716 A2 | 12/2012 |

OTHER PUBLICATIONS

Targett-Adams, P., et al., "Small Molecules Targeting Hepatitis C Virus—Encoded NS5A Cause Subcellular Redistribution of their Target: Insights into Compound Mode of Action", "J. Virol.", Apr. 20, 2011, pp. 6353-6368, vol. 85, No. 13.

Schmitz, U., et al., "NS5A—From Obscurity to New Target for HCV Therapy", "Recent Patents on Anti-Infective Drug Discovery", Jun. 2008, pp. 77-93, vol. 3, No. 2.

European Search Report for Application No. 15175835.6-1462 dated Oct. 7, 2015.

\* cited by examiner

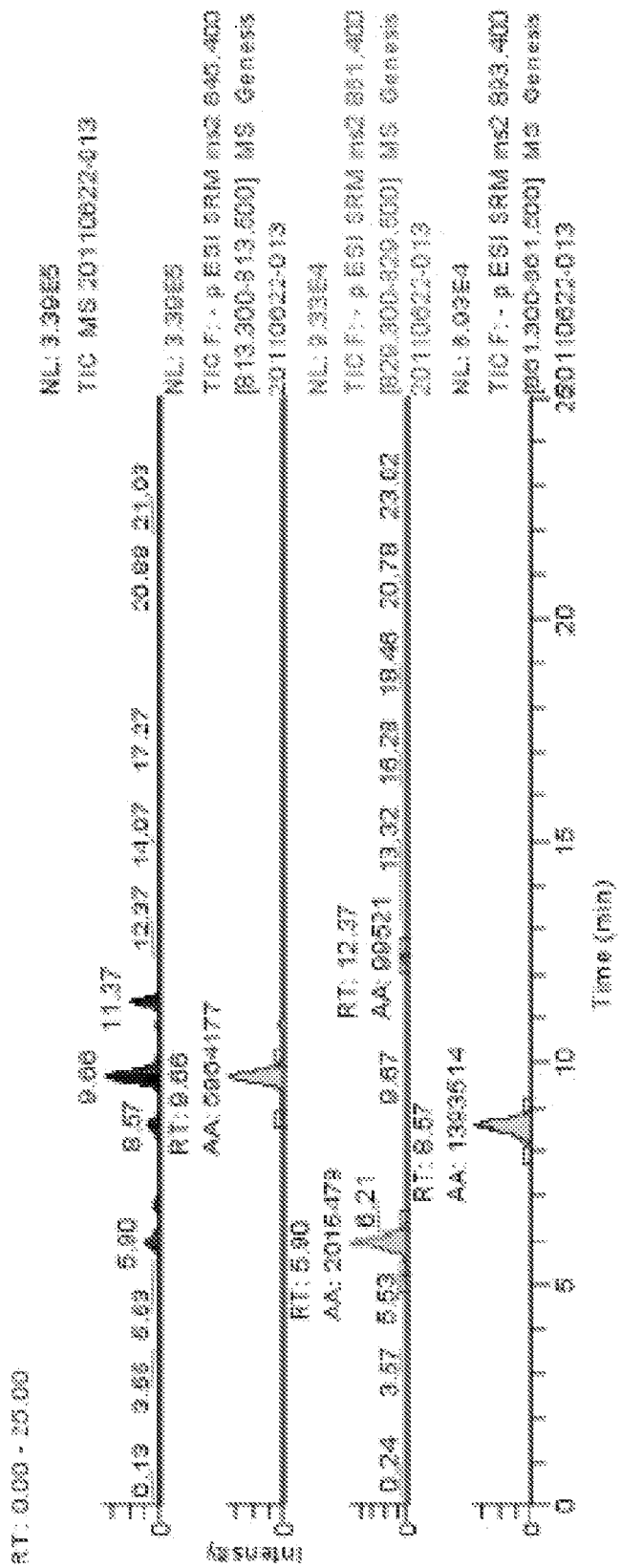

POTENT AND SELECTIVE INHIBITORS OF HEPATITIS C VIRUS

CROSS-REFERENCE TO RELATED APPLICATIONS

This is a continuation under 35 USC 120 of U.S. patent application Ser. No. 14/455,197 filed Aug. 8, 2014, which in turn is a continuation under 35 USC 120 of U.S. patent application Ser. No. 13/817,522 filed Feb. 18, 2013, which in turn is a national phase entry under the provisions of 35 U.S.C. § 371 of International Patent Application No. PCT/US11/49426 filed Aug. 26, 2011, which in turn claims priority of U.S. Provisional Patent Application No. 61/377,452 filed Aug. 26, 2010 and U.S. Provisional Patent Application No. 61/494,877 filed Jun. 8, 2011. The disclosures of all of said U.S. patent application Ser. No. 14/455,197, U.S. patent application Ser. No. 13/817,522, International Patent Application No. PCT/US11/49426 and U.S. Provisional Patent Application Nos. 61/377,452 and 61/494,877 are hereby incorporated herein by reference, in their respective entireties, for all purposes.

FIELD OF THE INVENTION

The present invention is directed to compounds, methods and compositions for treating or preventing hepatitis C virus (HCV) infections. More specifically, the invention describes specifically substituted aromatic compounds, pharmaceutically acceptable salts, or other derivatives thereof, and the use thereof in the treatment of HCV infection. Most of these compounds target the HCV NS5A phosphoprotein.

BACKGROUND OF THE INVENTION

Hepatitis C virus (HCV) has infected more than 180 million people worldwide. It is estimated that three to four million persons are newly infected each year, 70% of whom will develop chronic hepatitis. HCV is responsible for 50-76% of all liver cancer cases, and two thirds of all liver transplants in the developed world. Standard therapy [pegylated interferon alfa plus ribavirin (a nucleoside analog)] is only effective in 50-60% of patients and is associated with significant side-effects. Therefore, there is an urgent need for new HCV drugs.

Hepatitis C virus genome comprises a positive-strand RNA enclosed in a nucleocapsid and lipid envelope and consists of 9.6 kb ribonucleotides and has a single open reading frame (ORP) encoding which encodes a large polypeptide of about 3000 amino acids (Dymock et al. Antiviral Chemistry & Chemotherapy 2000, 11, 79). Following maturation, this polypeptide is cut into at least 10 proteins by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases: 1) a metalloprotease that cleaves at the NS2-NS3 junction; and 2) a serine protease contained within the N-terminal region of NS3 (NS3 protease) which mediates all the subsequent cleavages downstream of NS3. The NS4A protein appears to serve multiple functions including the NS4A/NS3 complex formation, which appears to enhance the proteolytic efficiency of the NS3 protein. NS5B (also referred to herein as HCV polymerase), possesses polymerase activity and is involved in the synthesis of double-stranded RNA from the single-stranded viral RNA genome that serves as the template. NS5A is a nonstructural 56-58 kDa protein which modulates HCV replication as a component of replication complex. NS5A is highly phosphorylated by cellular protein kinases and the phosphorylation sites are conserved among HCV genotypes (Katze et al, 2001; Kim et al, 1999)

The discovery of novel antiviral strategies to selectively inhibit HCV replication has long been hindered by the lack of convenient cell culture models for the propagation of HCV ("Recent Advances in Nucleoside Monophosphate Prodrugs as Anti-hepatitis C Virus Agents" Bobeck, D. R.; Coats, S. J.; Schinazi, R. F. Antivir. Ther. 2010; Book Chapter: "Approaches for the Development of Antiviral Compounds: The Case of Hepatitis C Virus." Raymond F. Schinazi, Steven J. Coats, Leda C. Bassit, Johan Lennerstrand, James H. Nettles, and Selwyn J. Hurwitz in: Handbook of Experimental Pharmacology, vol. 189, 25-51: Antiviral Strategies; Edited by: Hans-Georg Kräusslich and Ralf Bartenschlager © Springer-Verlag Berlin Heidelberg 2009). This hurdle has been overcome first with the establishment of the HCV replicon system in 1999 (Bartenschlager, R., Nat. Rev. Drug Discov. 2002, 1, 911-916 and Bartenschlager, R., J. Hepatol. 2005, 43, 210-216) and, in 2005, with the development of robust HCV cell culture models (Wakita, T., et al., Nat. Med. 2005, 11, 791-6; Zhong, J., et al., Proc. Natl. Acad. Sci. U.S.A. 2005, 102, 9294-9; Lindenbach, B. D., et al., Science 2005, 309, 623-6).

It would be advantageous to provide new antiviral agents, compositions including these agents, and methods of treatment using these agents, particularly to treat HCV and drug-resistant HCV. The present invention provides such agents, compositions and methods.

SUMMARY OF THE INVENTION

The present invention provides compounds, methods and compositions for treating or preventing HCV infection in a host. The methods involve administering a therapeutically or prophylactically-effective amount of at least one compound as described herein to treat or prevent an infection by, or an amount sufficient to reduce the biological activity of HCV infection. The pharmaceutical compositions include one or more of the compounds described herein, in combination with a pharmaceutically acceptable carrier or excipient, for treating a host infected with HCV. These compounds can be used in combination with nucleoside and non-nucleoside inhibitors of HCV. The formulations can further include at least one other therapeutic agent. In addition, the present invention includes processes for preparing such compounds.

In one embodiment, the active compound is of formula (I):

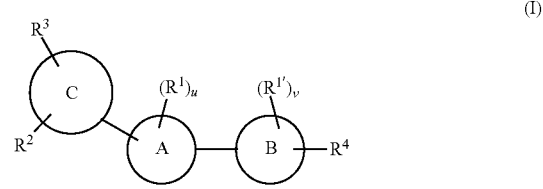

or a pharmaceutically acceptable salt thereof, wherein each $R^1$ and $R^{1'}$ is present or absent if present is independently selected from hydroxy, hydroxyalkyl, alkoxy($C_{1-6}$), alkoxyalkyl($C_{2-8}$), alkoxycarbonyl, alkyl($C_{1-8}$), arylalkoxycarbonyl, lower alkenyl ($C_{2-6}$), lower alkynyl ($C_{2-6}$), carboxy, halogen (F, Cl, Br, I), haloalkyl, $CF_3$, $N_3$, CN, $N(R')_2$, SR', OCOR', N(COR')R', N(COR')COR', SCOR', $S(O)_2$ NR'$_2$, S(O)$_2$R'. Each R' is independently H, a lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower cycloalkyl (C$_{3-6}$), aryl, heteroaryl, alkylaryl, arylalkyl, or if two R' reside on the same nitrogen atom they can come together to form an alkyl ring (C$_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;

A is selected from phenyl and six-membered heteroaromatic rings containing one, two, or three nitrogen atoms;

B is cyclic or acyclic

If B is cyclic it is selected from phenyl and a six-membered heteroaromatic ring containing one, two, or three nitrogen atoms, a six-membered ring or a six-membered bridged or spiro-fused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;

If B is acyclic R$^4$ and R$^{1'}$ are absent and B is selected from halogen (F, Cl, Br, I), OR', CF$_3$, N$_3$, CN, N(R')$_2$, SR', OCOR', N(COR')R', N(COR')COR', SCOR', S(O)$_2$NR'$_2$, S(O)$_2$R', N(R')S(O)$_2$R', lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower allenyl (C$_{3-6}$). Each R' is as defined above.

C is a five-membered heteroaromatic ring containing one, two or three heteroatoms selected from nitrogen, sulfur, and oxygen.

When R$^2$ is attached to a carbon it is selected from hydrogen, halogen (F, Cl, Br, I), CF$_3$, N(R')S(O)$_2$R', S(O)$_2$R', S(O)$_2$N(R')$_2$, hydroxy, alkoxy (C$_{1-6}$), cyano, alkynyl (C$_{2-6}$), alkoxyalkyl (C$_{3-6}$), alkoxycarbonyl, alkoxycarbonylalkyl, alkyl, arylalkoxycarbonyl, carboxy, haloalkyl, heterocyclylalkyl, hydroxyalkyl;

When R$^2$ is attached to a nitrogen it is selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$), S(O)$_2$R';

R$^3$ is selected from

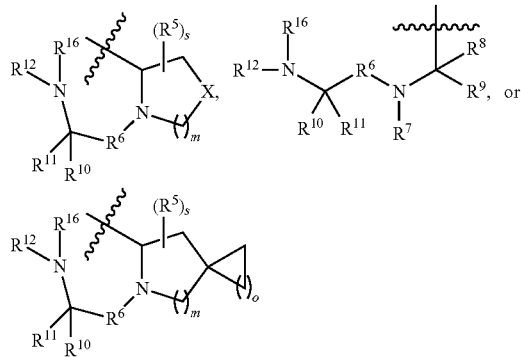

each m is independently 0, 1, or 2;
each o is independently 1, 2, or 3;
each s is independently 0, 1, or 2;

each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;

each R$^5$ is independently selected from alkoxy, alkyl, aryl, halogen (F, Cl, Br, I), CF$_3$, N$_3$, haloalkyl, hydroxy, with the proviso that C(R$^5$)$_2$ cannot be C(alkoxy)$_2$, C(OH)$_2$, C(alkoxy)(OH), or C(halo)(OH), and with the further proviso that C(R$^5$)$_2$ can also be C(O), each R$^6$ is independently selected from —C(O)—, —C(S)— and —C(NR$^z$)—;

R$^7$ is selected from hydrogen and alkyl;

R$^8$ and R$^9$ are each independently selected from hydrogen, alkenyl, alkoxyalkyl, alkyl, haloalkyl, and hydroxyalkyl; or, R$^8$ and R$^9$, together with the carbon atom to which they are attached, form a five- or six-membered saturated ring optionally containing one or two heteroatoms selected from NR$^z$, O, and S; wherein R$^z$ is selected from hydrogen and alkyl;

each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each R$^{12}$ and R$^{16}$ are independently selected from hydrogen, R$^{13}$—C(O)—, R$^{13}$—C(S)—, and R'; Each R' is as defined above;

each R$^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$, and R$^4$ is selected from halogen (F, Cl, Br, I), CF$_3$, OR', N$_3$, CN, N(R')$_2$, SR', OCOR', N(COR')R', N(COR')COR', SCOR', lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower allenyl (C$_{3-6}$), lower cycloalkyl (C$_3$-6) alkylheteroaryl, or alkylaryl. Each R' is as defined above.

The compounds described herein can be in the form of the R- or S-configuration, or a mixture thereof, including a racemic or diastereomeric mixture thereof.

In a second embodiment, the active compound is of formula (II):

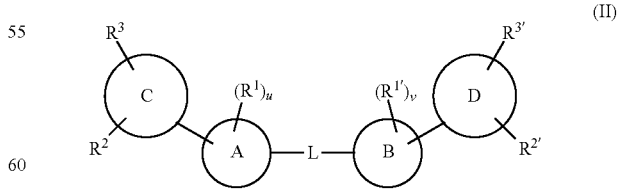

(II)

each R$^1$ and R$^{1'}$ are independently present or absent if present are independently selected from hydroxy, hydroxyalkyl, alkoxy(C$_{1-6}$), alkoxyalkyl(C$_{2-8}$), alkoxycarbonyl, alkyl(C$_{1-8}$), arylalkoxycarbonyl, lower alkenyl (C$_{2-6}$), lower alkynyl (C$_{2-6}$), carboxy, halogen (F, Cl, Br, I), CF$_3$, haloalkyl, $N_3$, CN, $N(R')_2$, SR', OCOR', N(COR')R', N(COR')COR', SCOR', $S(O)_2NR'_2$, $S(O)_2R'$. Each R' is independently H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, alkylaryl, arylalkyl, or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;

A is selected from phenyl and six-membered heteroaromatic rings containing one, two, or three nitrogen atoms;

B is selected from phenyl and a six-membered heteroaromatic ring containing one, two, or three nitrogen atoms, a six-membered ring or a six-membered bridged or spiro-fused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;

L is selected from O, S, S(O), $S(O)_2$, C=NCN, or selected from phenyl and a six-membered heteroaromatic ring containing one, two, or three nitrogen atoms, a six-membered ring or a six-membered bridged ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S;

Alternatively, L can be $C(R')_2$, and NR', where R' is as defined above.

C and D are independently a five-membered heteroaromatic ring containing one, two or three heteroatoms selected from nitrogen, sulfur, and oxygen;

When $R^2$ and $R^{2'}$ are attached to a carbon they are independently selected from hydrogen, halogen (F, Cl, Br, I), $CF_3$, $N(R')S(O)_2R'$, $S(O)_2R'$, $S(O)_2N(R')_2$, hydroxy, alkoxy ($C_{1-6}$), cyano, alkynyl ($C_{2-6}$), alkoxyalkyl ($C_{3-6}$), alkoxycarbonyl, alkoxycarbonylalkyl, alkyl, arylalkoxycarbonyl, carboxy, haloalkyl, heterocyclylalkyl, hydroxyalkyl;

When $R^2$ and $R^{2'}$ are attached to a nitrogen they are independently selected from hydrogen, alkoxy ($C_{2-6}$), alkoxyalkyl ($C_{3-6}$), alkoxycarbonyl, carbonylalkyl, carbonyl aryl, alkyl, heterocyclylalkyl, hydroxyalkyl ($C_{2-6}$), $S(O)_2R'$;

$R^3$ and $R^{3'}$ are independently selected from

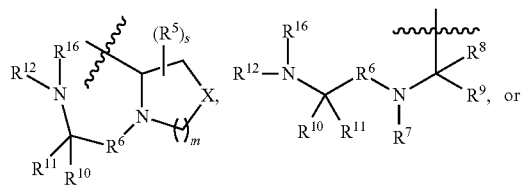

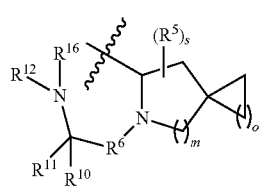

each m is independently 0, 1, or 2;
each o is independently 1, 2, or 3;
each s is independently 0, 1, 2, or 3;
each X is independently selected from O, S, S(O), $SO_2$, $CH_2$, $CHR^5$, and $C(R^5)_2$; provided that when m is 0, X is selected from $CH_2$, $CHR^5$, and $C(R^5)_2$;
each $R^5$ is independently selected from $CF_3$, $N_3$, and haloalkyl, with the proviso that $C(R^5)_2$ can also be C(O),
each $R^6$ is independently selected from —C(O)—, —C(S)— and —C(NR$^z$)—;
$R^7$ is selected from hydrogen and alkyl;
$R^8$ and $R^9$ are each independently selected from hydrogen, alkenyl, alkoxyalkyl, alkyl, haloalkyl, and hydroxyalkyl; or, $R^8$ and $R^9$, together with the carbon atom to which they are attached, form a five- or six-membered saturated ring optionally containing one or two heteroatoms selected from $NR^z$, O, and S; wherein $R^z$ is selected from hydrogen and alkyl;
each $R^{10}$ and $R^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;
each $R^{12}$ and $R^{16}$ are independently selected from hydrogen, $R^{13}$—C(O)—, $R^{13}$—C(S)—, and R'; Each R' is as defined above; and
each $R^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —$N(R')_2$. Each R' is as defined above.

The compounds described herein can be in the form of the R- or S-configuration, or a mixture thereof, including a racemic or diastereomeric mixture thereof.

In a third embodiment, the active compound is of formula (III):

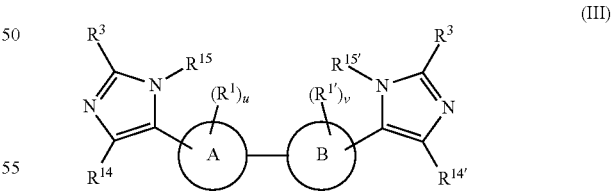

each $R^1$ and $R^{1'}$ is present or absent if present is independently selected from hydroxy, hydroxyalkyl, alkoxy($C_{1-6}$), alkoxyalkyl($C_{2-8}$), alkoxycarbonyl, alkyl($C_{1-8}$), arylalkoxycarbonyl, lower alkenyl ($C_{2-6}$), lower alkynyl ($C_{2-6}$), carboxy, halogen (F, Cl, Br, I), $CF_3$, haloalkyl, $N_3$, CN, $N(R')_2$, SR', OCOR', N(COR')R', N(COR')COR', SCOR', $S(O)_2NR'_2$, $S(O)_2R'$. Each R' is independently H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, alkylaryl, arylalkyl, or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;

A is selected from phenyl and six-membered heteroaromatic rings containing one, two, or three nitrogen atoms;

B is selected from phenyl and a six-membered heteroaromatic ring containing one, two, or three nitrogen atoms, a six-membered ring or a six-membered bridged or spiro-fused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;

$R^3$ is selected from

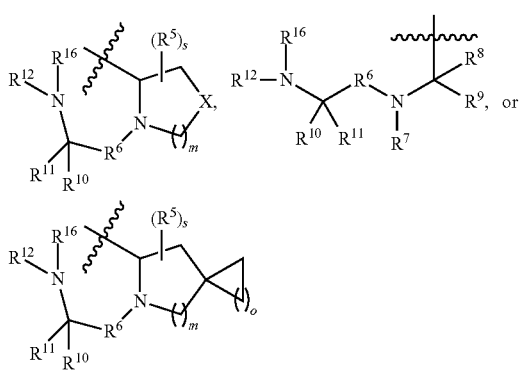

each m is independently 0, 1, or 2;
each o is independently 1, 2, or 3;
each s is independently 0, 1, 2, or 3;
each X is independently selected from O, S, S(O), $SO_2$, $CH_2$, $CHR^5$, and $C(R^5)_2$; provided that when m is 0, X is selected from $CH_2$, $CHR^5$, and $C(R^5)_2$;
each $R^5$ is independently selected from $CF_3$, $N_3$, and haloalkyl, with the proviso that $C(R^5)_2$ can also be C(O), each $R^6$ is independently selected from —C(O)—, —C(S)— and —C($NR^z$)—;

$R^7$ is selected from hydrogen and alkyl;

$R^8$ and $R^9$ are each independently selected from hydrogen, alkenyl, alkoxyalkyl, alkyl, haloalkyl, and hydroxyalkyl; or, $R^8$ and $R^9$, together with the carbon atom to which they are attached, form a five- or six-membered saturated ring optionally containing one or two heteroatoms selected from $NR^z$, O, and S; wherein $R^z$ is selected from hydrogen and alkyl;

each $R^{10}$ and $R^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each $R^{12}$ and $R^{16}$ are independently selected from hydrogen, $R^{13}$—C(O)—, $R^{13}$—C(S)—, and R'; Each R' is as defined above;

each $R^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$. Each R' is as defined above.

$R^{14}$ and $R^{14'}$ are independently selected from halogen (F, Cl, Br, I), $CF_3$, hydroxy, alkoxy ($C_{1-6}$), cyano, alkynyl ($C_{2-6}$), alkoxyalkyl ($C_{3-6}$), alkoxycarbonylalkyl, alkyl, arylalkoxycarbonyl, carboxy, haloalkyl, heterocyclylalkyl, hydroxyalkyl; and $R^{15}$ and $R^{15'}$ are independently selected from hydrogen, alkoxy ($C_{2-6}$), alkoxyalkyl ($C_{3-6}$), alkoxycarbonyl, carbonylalkyl, carbonyl aryl, alkyl, heterocyclylalkyl, hydroxyalkyl ($C_{2-6}$).

The compounds described herein can be in the form of the R- or S-configuration, or a mixture thereof, including a racemic or diastereomeric mixture thereof.

Representative compounds include the following:

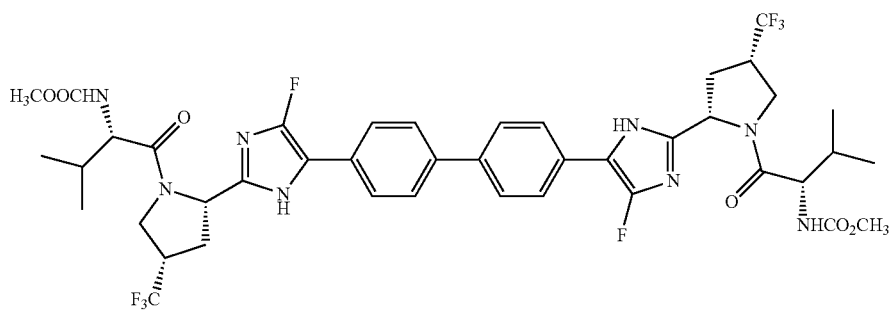

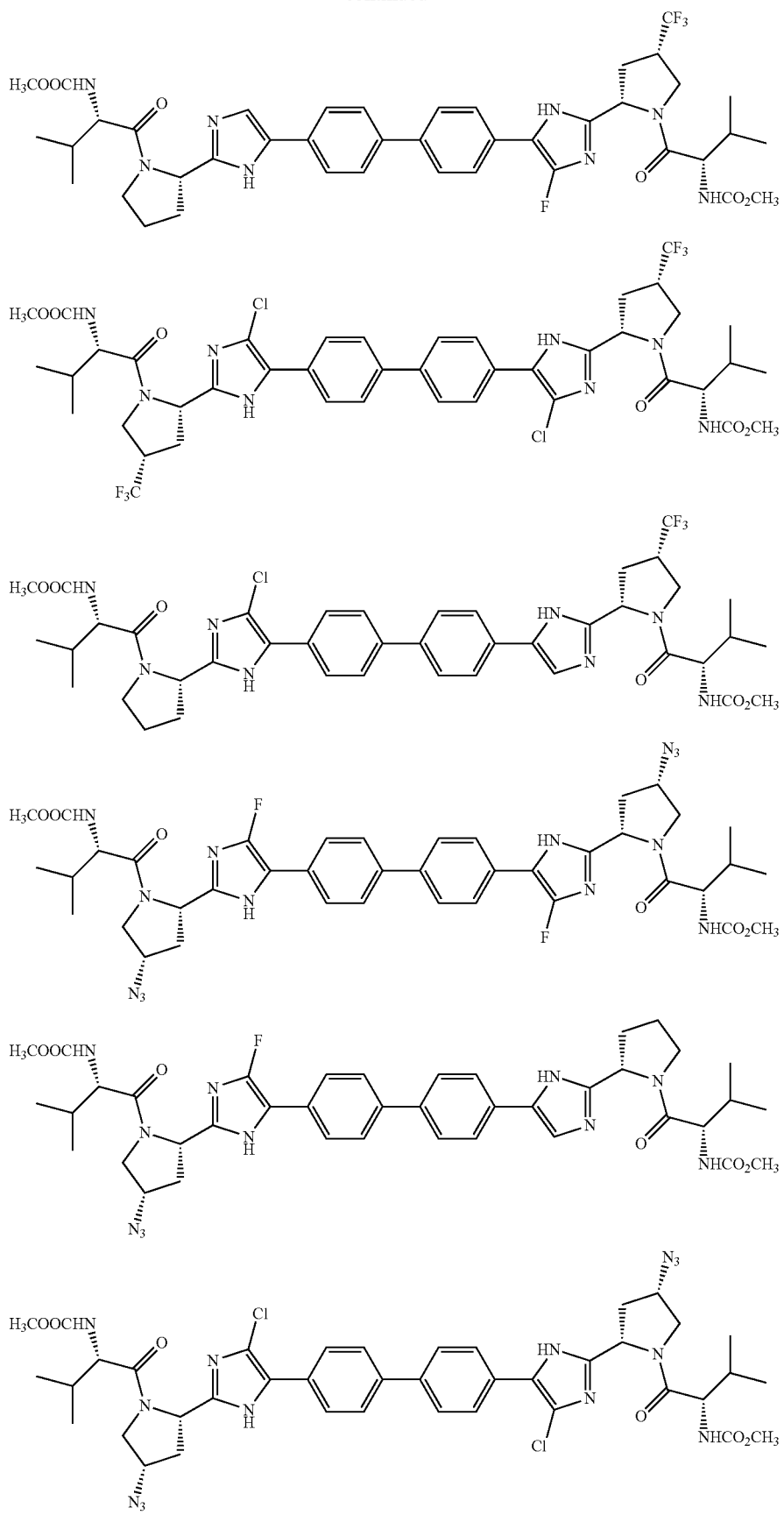

-continued

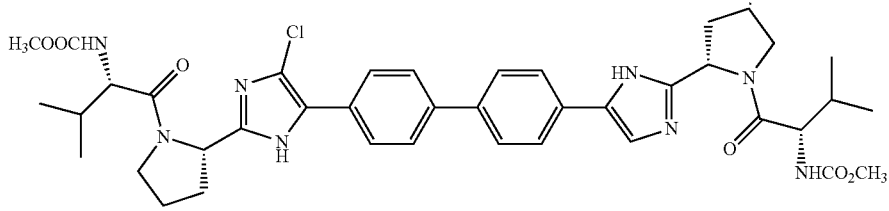

In a fourth embodiment, the compounds have the following formula:

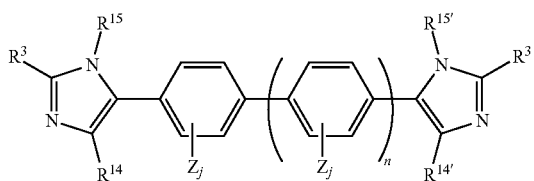

wherein:

R³ is

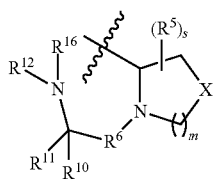

each m is independently 0, 1, or 2;

n is 0, 1, 2, or 3, each s is independently 0, 1, 2, or 3;

each X is independently selected from O, S, S(O), $SO_2$, $CH_2$, $CHR^5$, and $C(R^5)_2$; provided that when m is 0, X is selected from $CH_2$, $CHR^5$, and $C(R^5)_2$;

each $R^5$ is independently selected from 5-membered heteroaryl, halo substituted 5-membered heteroaryl, thioalkyl, thioaryl, $SCH_3$, $SCF_3$, sulfoxide alkyl, sulfoxide aryl, S(O)$CH_3$, $S(O)CF_3$, sulfone alkyl, sulfone aryl, $S(O)_2CH_3$, $S(O)_2CF_3$, haloalkyl, $CF_3$, $N_3$, and CN.

with the proviso that $C(R^5)_2$ can also be C(O), each $R^6$ is independently selected from —C(O)—, —C(S)— and —C($NR^z$)—;

each $R^{10}$ and $R^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each $R^{12}$ and $R^{16}$ are independently selected from hydrogen, $R^{13}$—C(O)—, $R^{13}$—C(S)—, and R'; Each R' is as defined above;

each $R^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')₂, wherein each R' is as defined above;

$R^{14}$ and $R^{14'}$ are independently selected from halogen (F, Cl, Br, I), $CF_3$, hydroxy, alkoxy ($C_{1-6}$), aryl, 5-membered heteroaryl, lower alkyl ($C_{1-6}$) or halo substituted aryl, aryl or halo substituted 5-membered heteroaryl, cyano, alkynyl ($C_{2-6}$), alkoxyalkyl ($C_{3-6}$), alkoxycarbonylalkyl, alkyl, arylalkoxycarbonyl, carboxy, haloalkyl, heterocyclylalkyl, hydroxyalkyl; and $R^{15}$ and $R^{15'}$ are independently selected from hydrogen, alkoxy ($C_{2-6}$), alkoxyalkyl ($C_{3-6}$), alkoxycarbonyl, carbonylalkyl, carbonyl aryl, alkyl, heterocyclylalkyl, hydroxyalkyl ($C_{2-6}$), and pharmaceutically acceptable salts and prodrugs thereof, Z is $C_{1-6}$ alkyl (including cycloalkyl), alkenyl, heterocyclyl, aryl, heteroaryl, halo (e.g., F, Cl, Br, or I), —OR', —NR'R", —$CF_3$, —CN, —$NO_2$, —$C_2R'$, —SR', —$N_3$, —C(=O)NR'R", —NR'C(=O)R", —C(=O)R', —C(=O)OR', —OC(=O)R', —OC(=O)NR'R", —NR'C(=O)OR", —$SO_2R'$, —$SO_2NR'R"$, and —$NR'SO_2R"$, where R' and R" are individually hydrogen, $C_{1-6}$ alkyl, cycloalkyl, heterocyclyl, aryl, or arylalkyl (such as benzyl), and j is an integer of from 0 to 3, wherein the compounds can be in the form of the R- or S-configuration, or a mixture thereof, including a racemic or diastereomeric mixture thereof.

In one aspect of this embodiment, the compounds have the following formula:

(IV)

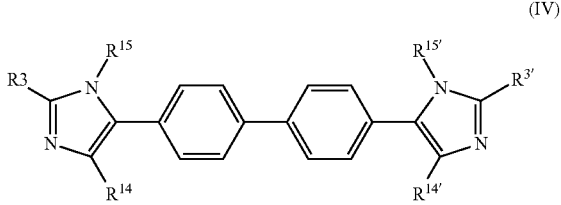

wherein:
R³ is

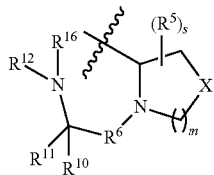

each m is independently 0, 1, or 2;

each s is independently 0, 1, or 2;

each s is independently 0, 1, 2, or 3;

each X is independently selected from O, S, S(O), SO$_2$, CH$_2$, CHR⁵, and C(R⁵)$_2$; provided that when m is 0, X is selected from CH$_2$, CHR⁵, and C(R⁵)$_2$;

each R⁵ is independently selected from 5-membered heteroaryl, halo substituted 5-membered heteroaryl, thioalkyl, thioaryl, SCH$_3$, SCF$_3$, sulfoxide alkyl, sulfoxide aryl, S(O)CH$_3$, S(O)CF$_3$, sulfone alkyl, sulfone aryl, S(O)$_2$CH$_3$, S(O)$_2$CF$_3$, haloalkyl, CF$_3$, N$_3$, and CN.

with the proviso that C(R⁵)$_2$ can also be C(O), each R⁶ is independently selected from —C(O)—, —C(S)— and —C(NR$^z$)—;

each R¹⁰ and R¹¹ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each R¹² and R¹⁶ are independently selected from hydrogen, R¹³—C(O)—, R¹³—C(S)—, and R'; Each R' is as defined above;

each R¹³ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$, wherein each R' is as defined above;

R¹⁴ and R¹⁴' are independently selected from halogen (F, Cl, Br, I), CF$_3$, hydroxy, alkoxy (C$_{1-6}$), aryl, 5-membered heteroaryl, lower alkyl (C$_{1-6}$) or halo substituted aryl, aryl or halo substituted 5-membered heteroaryl, cyano, alkynyl (C$_{2-6}$), alkoxyalkyl (C$_{3-6}$), alkoxycarbonylalkyl, alkyl, arylalkoxycarbonyl, carboxy, haloalkyl, heterocyclylalkyl, hydroxyalkyl; and R¹⁵ and R¹⁵' are independently selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$), and pharmaceutically acceptable salts and prodrugs thereof, wherein the compounds can be in the form of the R- or S-configuration, or a mixture thereof, including a racemic or diastereomeric mixture thereof.

The compounds described herein can be in the form of the R- or S-configuration, or a mixture thereof, including a racemic or diastereomeric mixture thereof.

Representative compounds include the following:

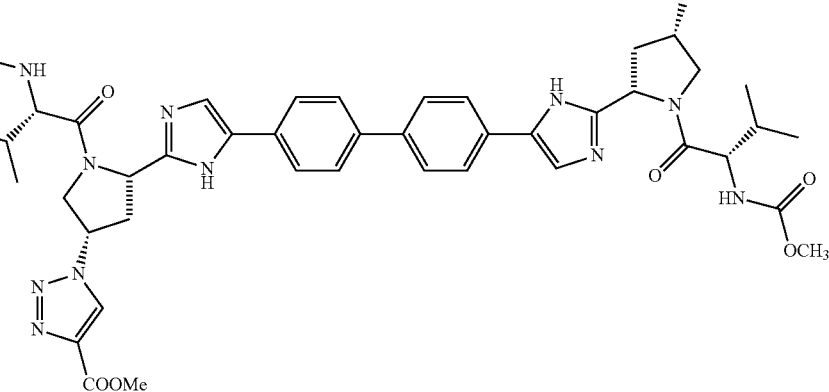

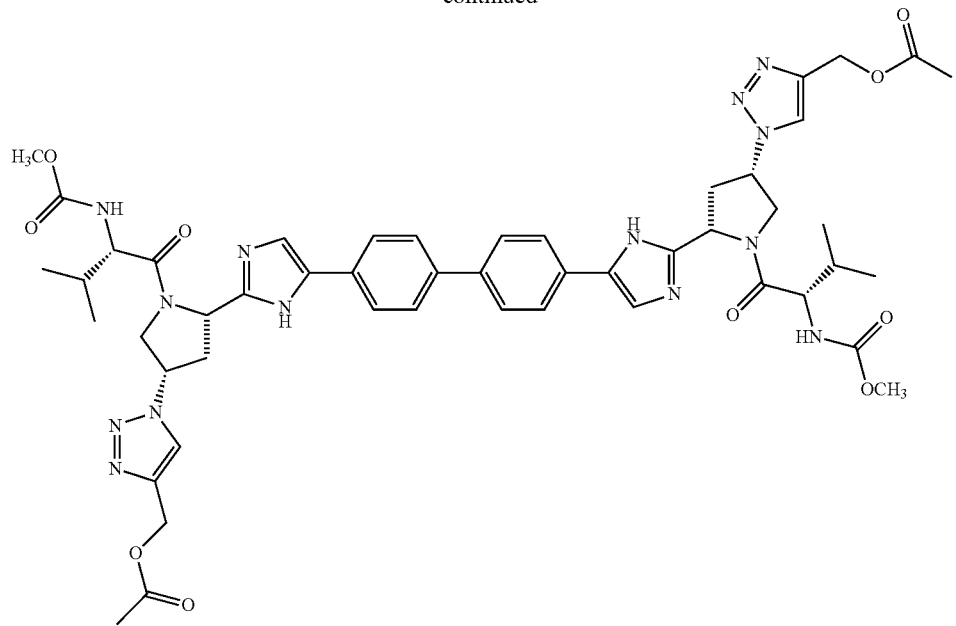
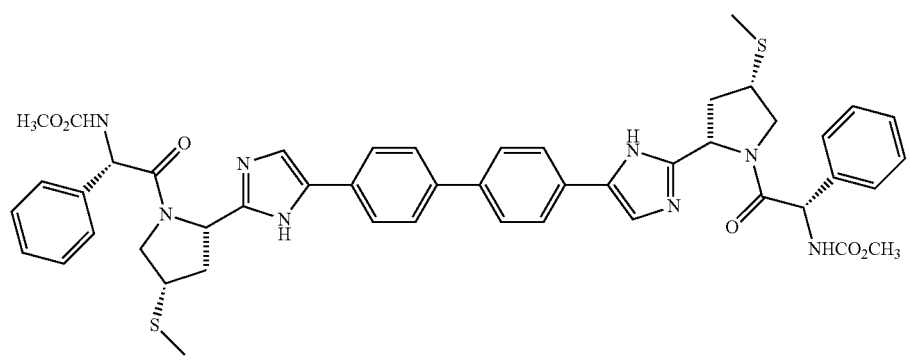
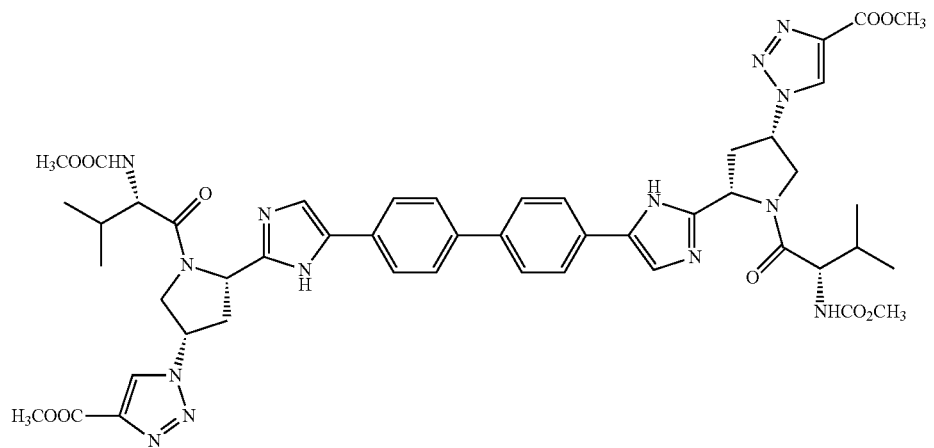

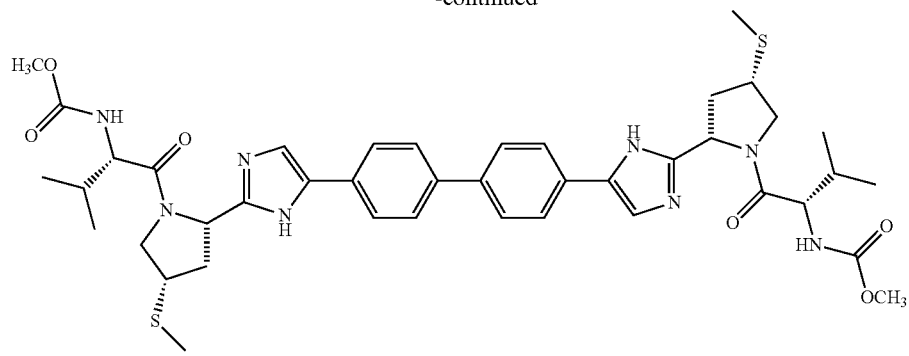
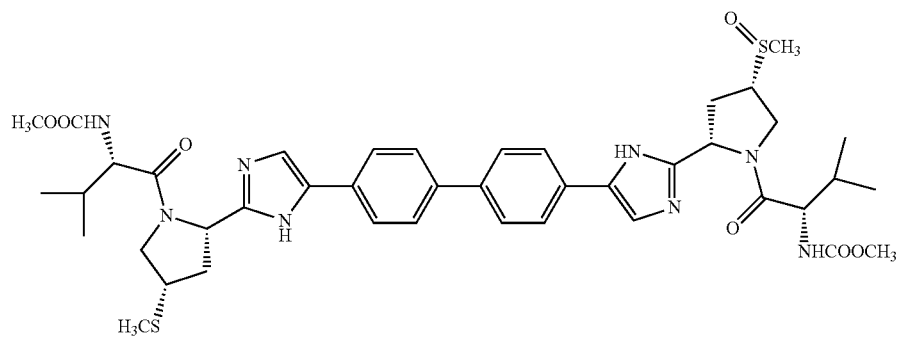
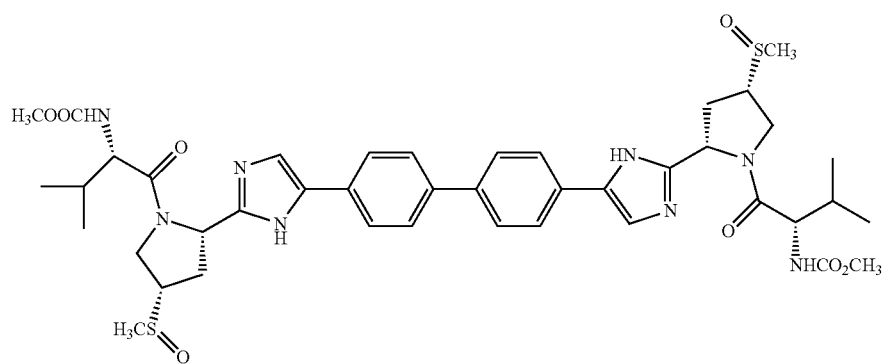
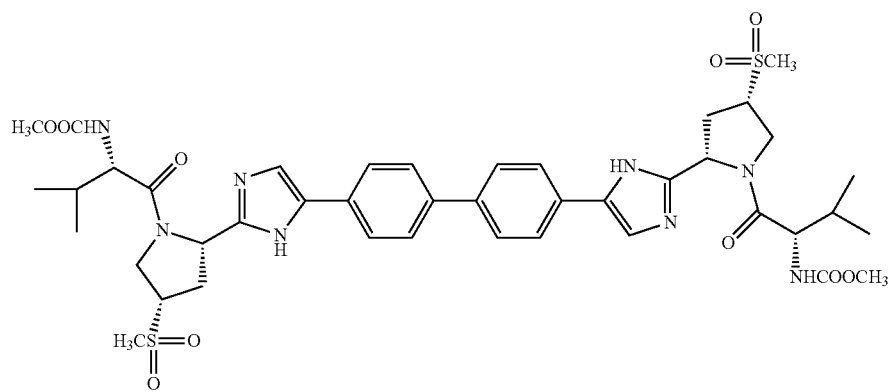

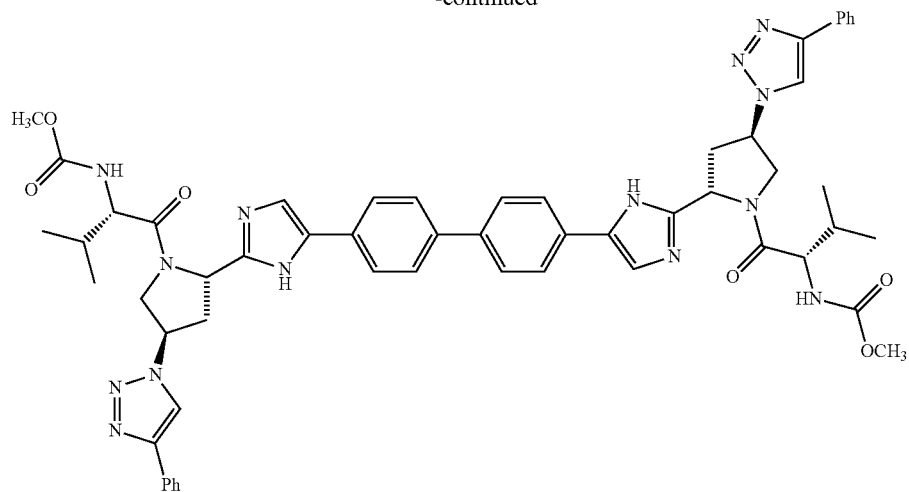
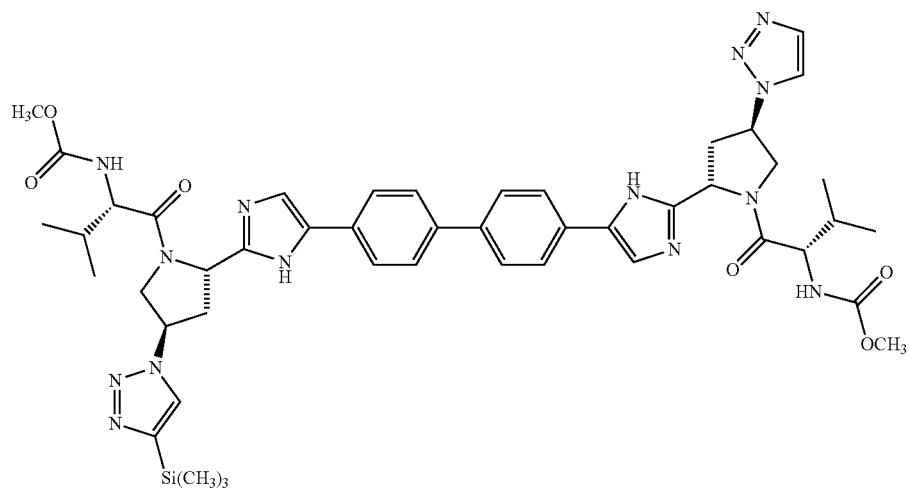
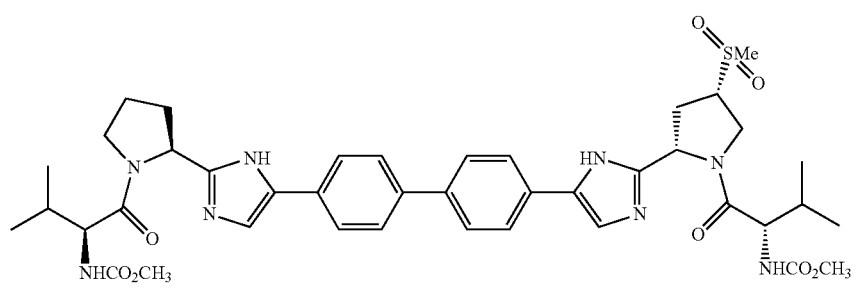
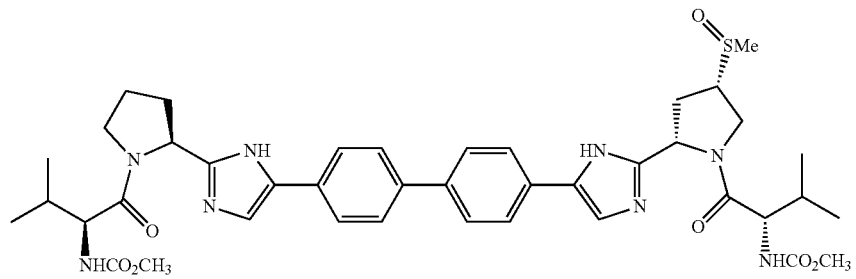

-continued
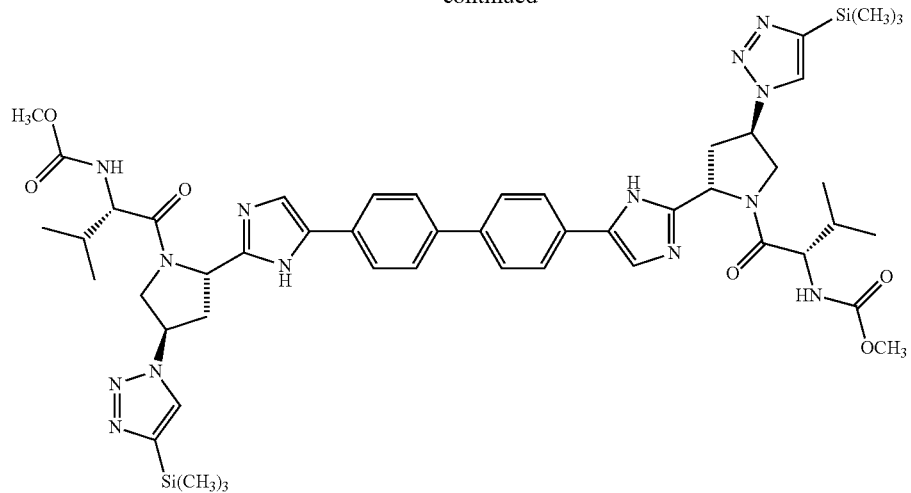
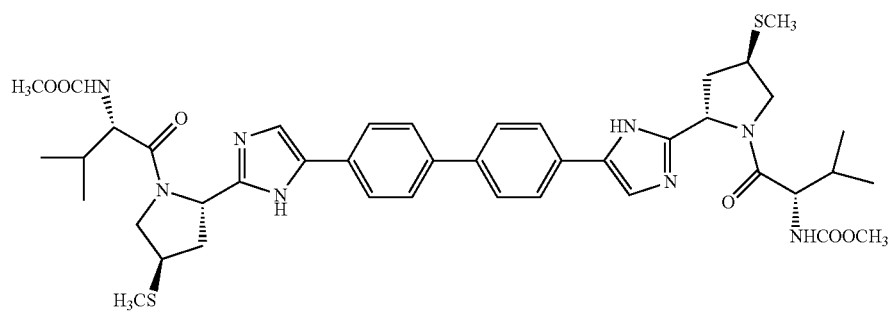
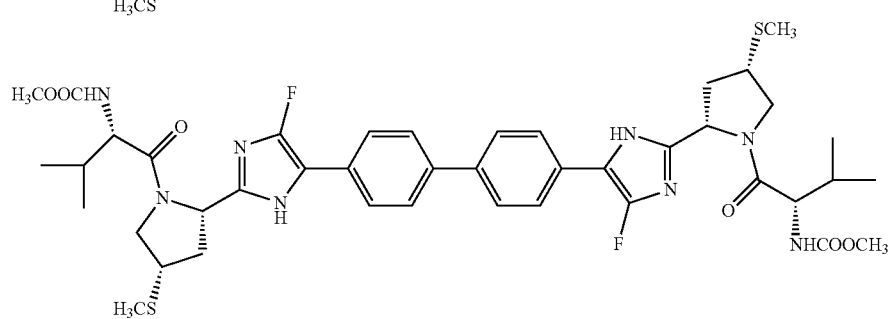
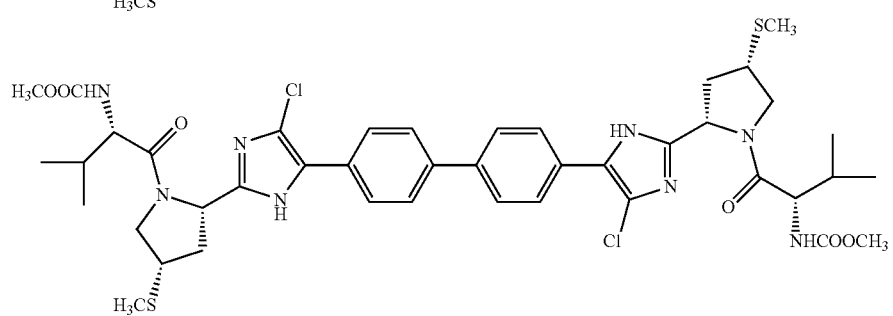
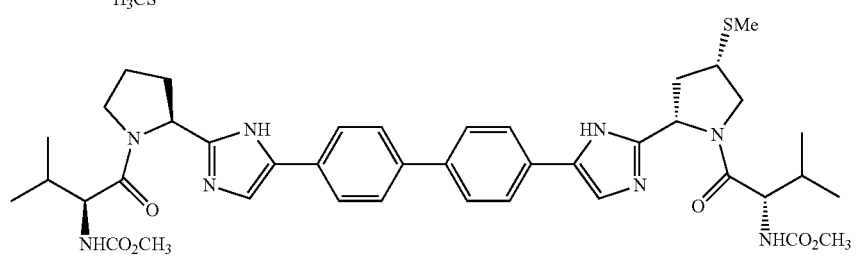

In one embodiment of the compounds of any of Formulas 1-3, ring C or D is imidazole.

In another embodiment of the compounds of any of Formulas 1-3, ring B is pyrrolidinyl.

In another embodiment of the compounds of any of Formulas 1-3, and ring A is phenyl or pyridinyl.

In still another embodiment of the compounds of any of Formulas 1-3, ring C or D is imidazole, ring B is pyrrolidinyl, and ring A is phenyl or pyridinyl.

The compounds can be used in combination therapy, for example, using conventional ribavirin/Pegasys therapy. Representative anti-HCV agents for use in combination therapy include, but are not limited to, a combination of Pegylated interferon (Pegasys) and ribavirin, polymerase inhibitors such as IDX-375 and IDX-184 (Idenix), PSI-7851 and PSI-7977 (Pharmasset) danoprevir (InterMune/Genentech), RG7128 (Pharmasset/Genentech), I ANA598 (Anadys Pharmaceuticals), TMN-191 (R7227), combinations of RG7128 and RG7227 (Genentech, Pharmasset and Intermune), ABT-072 (Abbott), VX-916, VX-759, VX-222, and VX-500 (Vertex), Filibuvir (PF-00868554) (Pfizer), GS 9190 (Gilead), alone or with boosters such as ritonavir, and serine protease inhibitors such as Boceprevir (SCH 503034) (Schering Plough), BILN-2061, Telaprevir (Vertex), ACH-1625 (Achillion), GS-9256 (Gilead), BI 201335 (Boehringer Ingelheim Pharma), Vaniprevir (MK-7009) (Merck), SCH900518 (Narlaprevir) (Schering/Merck), TMC435 (Medivir/Tibotec). Additional examples of serine protease inhibitors are provided, for example, in Reiser and Timm, "Serine protease inhibitors as anti-hepatitis C virus agents," Expert Review of Anti-infective Therapy, 7(5):537-547 (June 2009), the contents of which are hereby incorporated by reference.

The present invention will be better understood with reference to the following detailed description.

BRIEF DESCRIPTION OF THE DRAWINGS

FIG. 1 is a chromatogram of the mixture of Compound A and three standards, shown in terms of intensity versus time (min).

DETAILED DESCRIPTION

The compounds described herein show inhibitory activity against HCV in cell-based assays. Therefore, the compounds can be used to treat or prevent a HCV in a host, or reduce the biological activity of the virus. The host can be a mammal, and in particular, a human, infected with HCV. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compound

In one embodiment, the active compound is of formula (I):

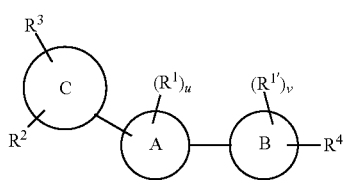

(I)

or a pharmaceutically acceptable salt thereof, wherein
each $R^1$ and $R^{1'}$ is present or absent if present is independently selected from hydroxy, hydroxyalkyl, alkoxy($C_{1-6}$), alkoxyalkyl($C_{2-8}$), alkoxycarbonyl, alkyl($C_{1-8}$), arylalkoxycarbonyl, lower alkenyl ($C_{2-6}$), lower alkynyl ($C_{2-6}$), carboxy, halogen (F, Cl, Br, I), $CF_3$, haloalkyl, $N_3$, CN, $N(R')_2$, SR', OCOR', N(COR')R', N(COR')COR', SCOR', $S(O)_2$ $NR'_2$, $S(O)_2R'$. Each R' is independently H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, alkylaryl, arylalkyl, or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;

A is selected from phenyl and six-membered heteroaromatic rings containing one, two, or three nitrogen atoms;

B is cyclic or acyclic

If B is cyclic it is selected from phenyl and a six-membered heteroaromatic ring containing one, two, or three nitrogen atoms, a six-membered ring or a six-membered bridged or spiro-fused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;

If B is acyclic $R^4$ and $R^{1'}$ are absent and B is selected from halogen (F, Cl, Br, I), $CF_3$, OR', $N_3$, CN, $N(R')_2$, SR', OCOR', N(COR')R', N(COR')COR', SCOR', $S(O)_2NR'_2$, $S(O)_2R'$, lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower allenyl ($C_{3-6}$). Each R' is as defined above.

C is a five-membered heteroaromatic ring containing one, two or three heteroatoms selected from nitrogen, sulfur, and oxygen.

When $R^2$ is attached to a carbon it is selected from hydrogen, halogen (F, Cl, Br, I), $CF_3$, hydroxy, $N(R')S(O)_2R'$, $S(O)_2R'$, $S(O)_2N(R')_2$, alkoxy ($C_{1-6}$), cyano, alkynyl ($C_{2-6}$), alkoxyalkyl ($C_{3-6}$), alkoxycarbonyl, alkoxycarbonylalkyl, alkyl, arylalkoxycarbonyl, carboxy, haloalkyl, heterocyclylalkyl, hydroxyalkyl;

When $R^2$ is attached to a nitrogen it is selected from hydrogen, alkoxy ($C_{2-6}$), alkoxyalkyl ($C_{3-6}$), alkoxycarbonyl, carbonylalkyl, carbonyl aryl, alkyl, heterocyclylalkyl, hydroxyalkyl ($C_{2-6}$), $S(O)_2R'$;

$R^3$ is selected from

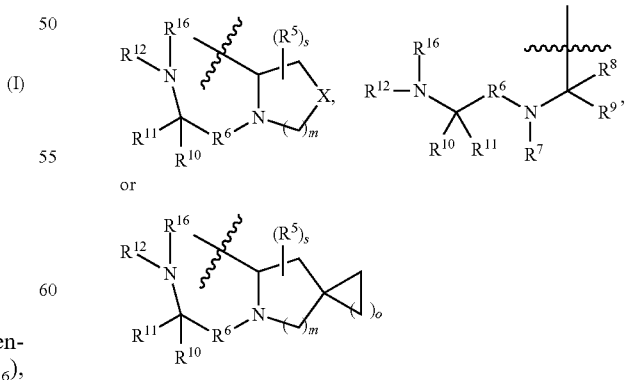

each m is independently 0, 1, or 2;
each o is independently 1, 2, or 3;
each s is independently 0, 1, 2, or 3;

each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;

each R$^5$ is independently selected from alkoxy, alkyl, aryl, halogen (F, Cl, Br, I), CF$_3$, N$_3$, haloalkyl, hydroxy, with the proviso that C(R$^5$)$_2$ cannot be C(alkoxy)$_2$, C(OH)$_2$, C(alkoxy)(OH), or C(halo)(OH), and with the further proviso that C(R$^5$)$_2$ can also be C(O), each R$^6$ is independently selected from —C(O)—, —C(S)— and —C(NR$^z$)—;

R$^7$ is selected from hydrogen and alkyl;

R$^8$ and R$^9$ are each independently selected from hydrogen, alkenyl, alkoxyalkyl, alkyl, haloalkyl, and hydroxyalkyl; or, R$^8$ and R$^9$, together with the carbon atom to which they are attached, form a five- or six-membered saturated ring optionally containing one or two heteroatoms selected from NR$^z$, O, and S; wherein R$^z$ is selected from hydrogen and alkyl;

each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each R$^{12}$ and R$^{16}$ are independently selected from hydrogen, R$^{13}$—C(O)—, R$^{13}$—C(S)—, and R'; Each R' is as defined above;

each R$^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$; and R$^4$ is selected from halogen (F, Cl, Br, I), CF$_3$, OR', N$_3$, CN, N(R')$_2$, SR', OCOR', N(COR')R', N(COR')COR', SCOR', lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower allenyl (C$_{3-6}$), lower cycloalkyl (C$_3$-6) alkylheteroaryl, or alkylaryl. Each R' is as defined above.

The compounds described herein can be in the form of the R- or S-configuration, or a mixture thereof, including a racemic or diastereomeric mixture thereof.

In a second embodiment, the active compound is of formula (II):

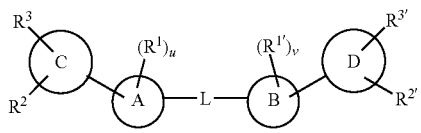

(II)

each R$^1$ and R$^{1'}$ are independently present or absent if present are independently selected from hydroxy, hydroxyalkyl, alkoxy(C$_{1-6}$), alkoxyalkyl(C$_{2-8}$), alkoxycarbonyl, alkyl(C$_{1-8}$), arylalkoxycarbonyl, lower alkenyl (C$_{2-6}$), lower alkynyl (C$_{2-6}$), carboxy, halogen (F, Cl, Br, I), CF$_3$, haloalkyl, N$_3$, CN, N(R')$_2$, SR', OCOR', N(COR')R', N(COR')COR', SCOR', S(O)$_2$NR'$_2$, S(O)$_2$R'. Each R' is independently H, a lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower cycloalkyl (C$_{3-6}$), aryl, heteroaryl, alkylaryl, arylalkyl, or if two R' reside on the same nitrogen atom they can come together to form an alkyl ring (C$_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;

A is selected from phenyl and six-membered heteroaromatic rings containing one, two, or three nitrogen atoms;

B is selected from phenyl and a six-membered heteroaromatic ring containing one, two, or three nitrogen atoms, a six-membered ring or a six-membered bridged or spiro-fused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;

L is selected from O, S, S(O), S(O)$_2$, C=NCN, or selected from phenyl and a six-membered heteroaromatic ring containing one, two, or three nitrogen atoms, a six-membered ring or a six-membered bridged ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S;

Alternatively, L can be C(R')$_2$, and NR', where R' is as defined above.

C and D are independently a five-membered heteroaromatic ring containing one, two or three heteroatoms selected from nitrogen, sulfur, and oxygen;

When R$^2$ and R$^{2'}$ are attached to a carbon they are independently selected from hydrogen, halogen (F, Cl, Br, I), CF$_3$, hydroxy, N(R')S(O)$_2$R', S(O)$_2$R', S(O)$_2$N(R')$_2$, alkoxy (C$_{1-6}$), cyano, alkynyl (C$_{2-6}$), alkoxyalkyl (C$_{3-6}$), alkoxycarbonyl, alkoxycarbonylalkyl, alkyl, arylalkoxycarbonyl, carboxy, haloalkyl, heterocyclylalkyl, hydroxyalkyl;

When R$^2$ and R$^{2'}$ are attached to a nitrogen they are independently selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$), S(O)$_2$R';

R$^3$ and R$^{3'}$ are independently selected from

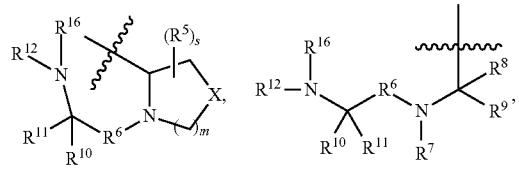

or

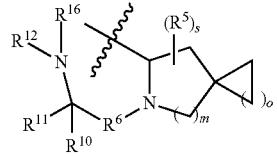

each m is independently 0, 1, or 2;
each o is independently 1, 2, or 3;
each s is independently 0, 1, 2, or 3;
each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;
each R$^5$ is independently selected from CF$_3$, N$_3$, and haloalkyl, with the proviso that C(R$^5$)$_2$ can also be C(O),
each R$^6$ is independently selected from —C(O)—, —C(S)— and —C(NR$^z$)—;
R$^7$ is selected from hydrogen and alkyl;
R$^8$ and R$^9$ are each independently selected from hydrogen, alkenyl, alkoxyalkyl, alkyl, haloalkyl, and hydroxyalkyl; or,
R$^8$ and R$^9$, together with the carbon atom to which they are attached, form a five- or six-membered saturated ring optionally containing one or two heteroatoms selected from NR$^z$, O, and S; wherein R$^z$ is selected from hydrogen and alkyl;
each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl
each R$^{12}$ and R$^{16}$ are independently selected from hydrogen, R$^{13}$—C(O)—, R$^{13}$—C(S)—, and R'; Each R' is as defined above; and
each R$^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$. Each R' is as defined above.

The compounds described herein can be in the form of the R- or S-configuration, or a mixture thereof, including a racemic or diastereomeric mixture thereof.

In a third embodiment, the active compound is of formula (III):

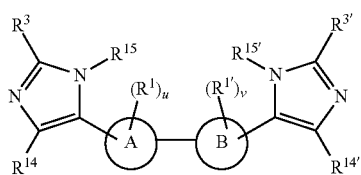

(III)

each R$^1$ and R$^{1'}$ is present or absent if present is independently selected from hydroxy, hydroxyalkyl, alkoxy(C$_{1-6}$), alkoxyalkyl(C$_{2-8}$), alkoxycarbonyl, alkyl(C$_{1-8}$), arylalkoxycarbonyl, lower alkenyl (C$_{2-6}$), lower alkynyl (C$_{2-6}$), carboxy, halogen (F, Cl, Br, I), CF$_3$, haloalkyl, N$_3$, CN, N(R')$_2$, SR', OCOR', N(COR')R', N(COR')COR', SCOR', S(O)$_2$NR'$_2$, S(O)$_2$R'. Each R' is independently H, a lower alkyl (C$_{1-6}$), lower haloalkyl (C$_{1-6}$), lower alkoxy (C$_{1-6}$), lower alkenyl (C$_{2-6}$), lower alkynyl (C$_{2-6}$), lower cycloalkyl (C$_{3-6}$), aryl, heteroaryl, alkylaryl, arylalkyl, or if two R' reside on the same nitrogen atom they can come together to form an alkyl ring (C$_{3-6}$) containing none or one heteroatom independently selected from N, O, and S; wherein the R' groups can be substituted with one or more substituents as defined above, for example, hydroxyalkyl, aminoalkyl, and alkoxyalkyl.

u and v are independently 0, 1, 2, 3, or 4;
A is selected from phenyl and six-membered heteroaromatic rings containing one, two, or three nitrogen atoms;
B is selected from phenyl and a six-membered heteroaromatic ring containing one, two, or three nitrogen atoms, a six-membered ring or a six-membered bridged or spirofused ring containing none, one, or two heteroatoms independently selected from N, O, and S, a five-membered heteroaromatic ring containing one, two, or three heteroatoms independently selected from N, O, and S, a five-membered ring containing none, one, or two heteroatoms independently selected from N, O, and S; a four-membered ring containing none, one, or two heteroatoms independently selected from N, O, and S; alkylheteroaryl, or alkylaryl;
R$^3$ is selected from

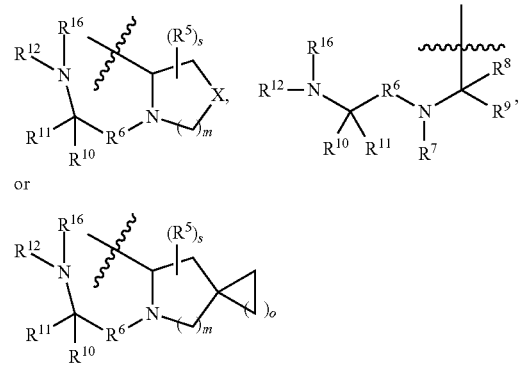

or each m is independently 0, 1, or 2;
each o is independently 1, 2, or 3;
each s is independently 0, 1, 2, or 3;
each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;
each R$^5$ is independently selected from CF$_3$, N$_3$, and haloalkyl, with the proviso that C(R$^5$)$_2$ can also be C(O),
each R$^6$ is independently selected from —C(O)—, —C(S)— and —C(NR$^z$)—;
R$^7$ is selected from hydrogen and alkyl;
R$^8$ and R$^9$ are each independently selected from hydrogen, alkenyl, alkoxyalkyl, alkyl, haloalkyl, and hydroxyalkyl; or,
R$^8$ and R$^9$, together with the carbon atom to which they are attached, form a five- or six-membered saturated ring optionally containing one or two heteroatoms selected from NR$^z$, O, and S; wherein R$^z$ is selected from hydrogen and alkyl;
each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl each $R^{12}$ and $R^{16}$ are independently selected from hydrogen, $R^{13}$—C(O)—, $R^{13}$—C(S)—, and R'; Each R' is as defined above;

each $R^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$. Each R' is as defined above.

$R^{14}$ and $R^{14'}$ are independently selected from halogen (F, Cl, Br, I), CF$_3$, hydroxy, alkoxy (C$_{1-6}$), cyano, alkynyl (C$_{2-6}$), alkoxyalkyl (C$_{3-6}$), alkoxycarbonylalkyl, alkyl, arylalkoxycarbonyl, carboxy, haloalkyl, heterocyclylalkyl, hydroxyalkyl; and $R^{15}$ and $R^{15'}$ are independently selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$).

The compounds described herein can be in the form of the R- or S-configuration, or a mixture thereof, including a racemic or diastereomeric mixture thereof.

Representative compounds include the following:

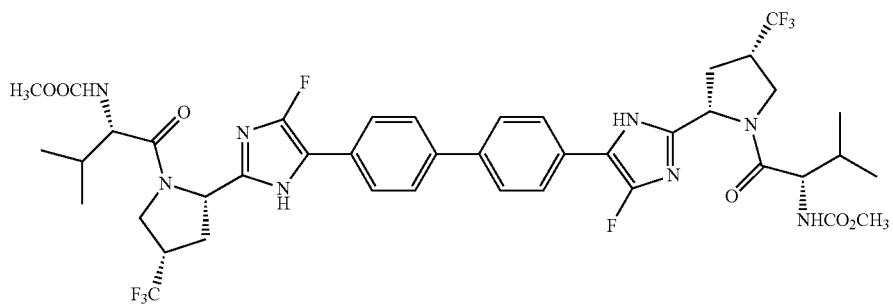

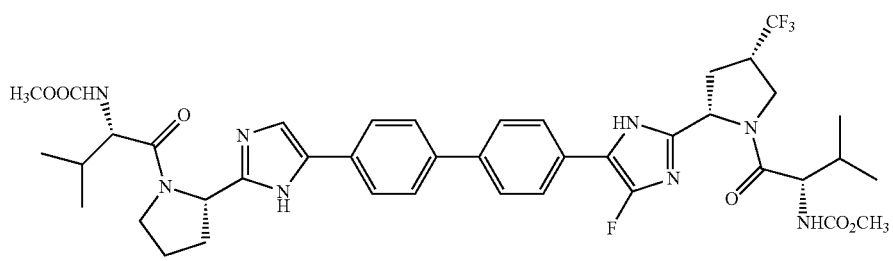

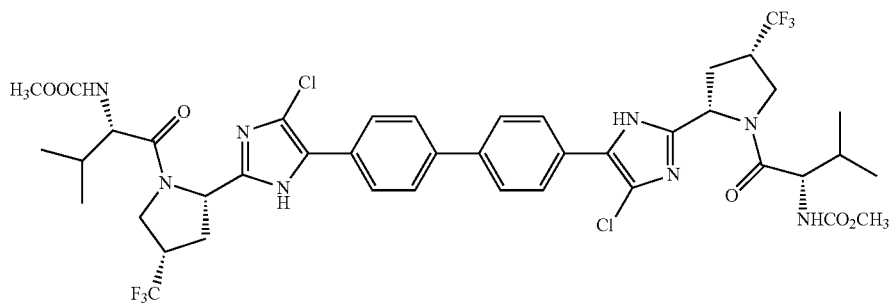

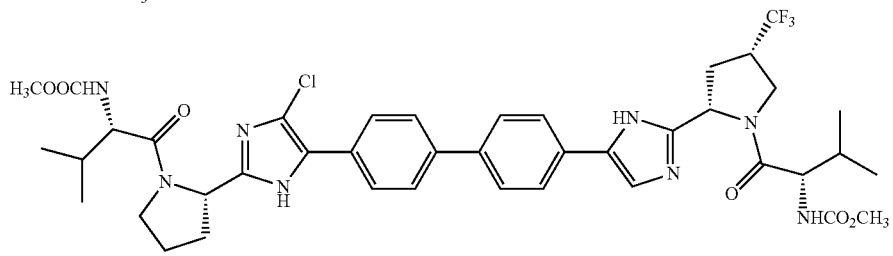

-continued

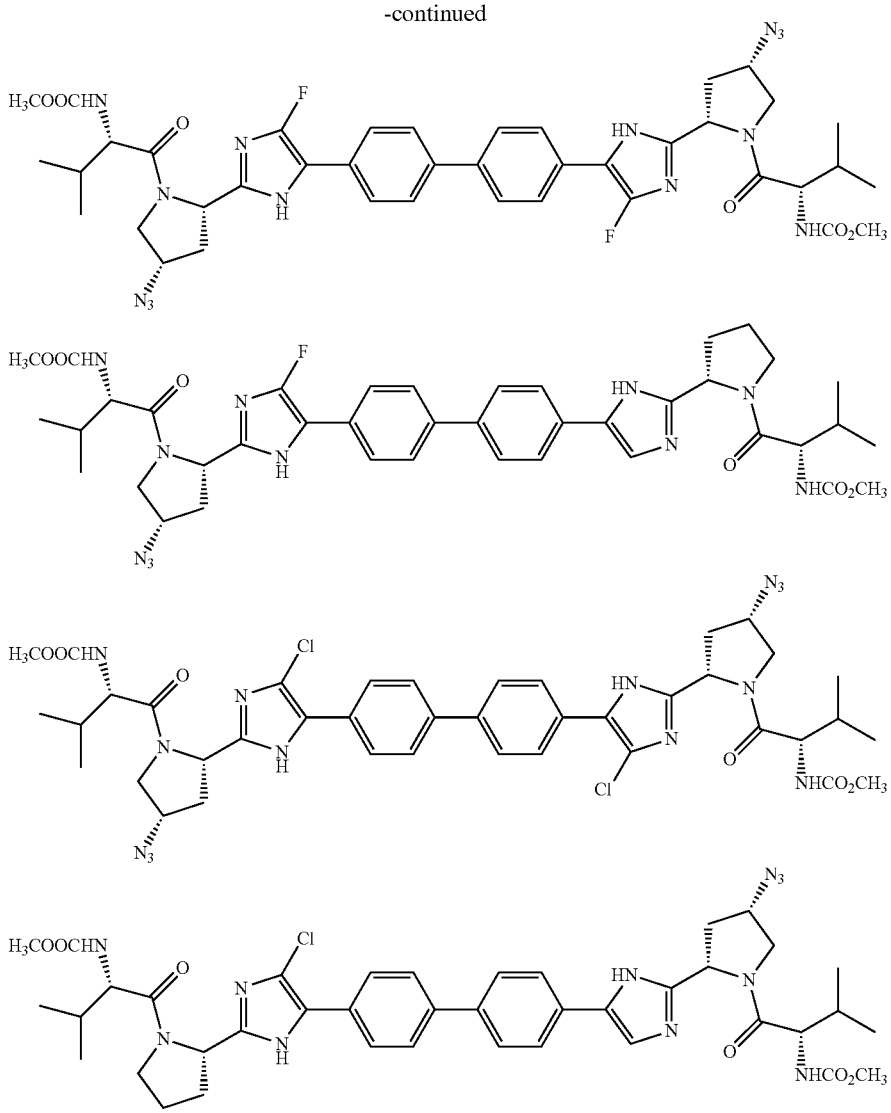

In a fourth embodiment, the compounds have the following formula:

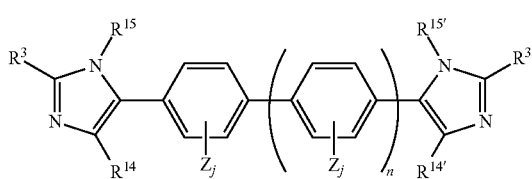

wherein:
R³ is

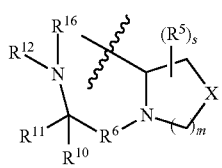

each m is independently 0, 1, or 2;
n is 0, 1, 2, or 3,
each s is independently 0, 1, 2, or 3;
each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;
each R$^5$ is independently selected from 5-membered heteroaryl, halo substituted 5-membered heteroaryl, thioalkyl, thioaryl, SCH$_3$, SCF$_3$, sulfoxide alkyl, sulfoxide aryl, S(O)CH$_3$, S(O)CF$_3$, sulfone alkyl, sulfone aryl, S(O)$_2$CH$_3$, S(O)$_2$CF$_3$, haloalkyl, CF$_3$, N$_3$, and CN.
with the proviso that C(R$^5$)$_2$ can also be C(O),
each R$^6$ is independently selected from —C(O)—, —C(S)— and —C(NR$^z$)—;
each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each $R^{12}$ and $R^{16}$ are independently selected from hydrogen, $R^{13}$—C(O)—, $R^{13}$—C(S)—, and R'; Each R' is as defined above;

each $R^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$, wherein each R' is as defined above;

$R^{14}$ and $R^{14'}$ are independently selected from halogen (F, Cl, Br, I), CF$_3$, hydroxy, alkoxy (C$_{1-6}$), aryl, 5-membered heteroaryl, lower alkyl (C$_{1-6}$) or halo substituted aryl, aryl or halo substituted 5-membered heteroaryl, cyano, alkynyl (C$_{2-6}$), alkoxyalkyl (C$_{3-6}$), alkoxycarbonylalkyl, alkyl, arylalkoxycarbonyl, carboxy, haloalkyl, heterocyclylalkyl, hydroxyalkyl; and $R^{15}$ and $R^{15'}$ are independently selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$), and pharmaceutically acceptable salts and prodrugs thereof, Z is C$_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O) R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl (such as benzyl), and j is an integer of from 0 to 3, wherein the compounds can be in the form of the R- or S-configuration, or a mixture thereof, including a racemic or diastereomeric mixture thereof.

In one aspect of this embodiment, the compounds have the following formula:

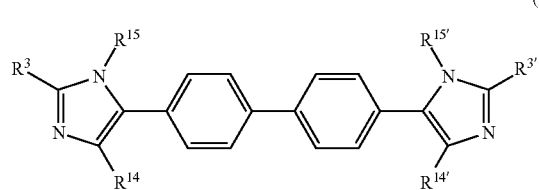

(IV)

wherein:
R$^3$ is

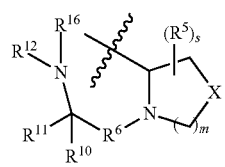

each m is independently 0, 1, or 2;
each s is independently 0, 1, 2, or 3;

each X is independently selected from O, S, S(O), SO$_2$, CH$_2$, CHR$^5$, and C(R$^5$)$_2$; provided that when m is 0, X is selected from CH$_2$, CHR$^5$, and C(R$^5$)$_2$;

each R$^5$ is independently selected from 5-membered heteroaryl, halo substituted 5-membered heteroaryl, thioalkyl, thioaryl, SCH$_3$, SCF$_3$, sulfoxide alkyl, sulfoxide aryl, S(O) CH$_3$, S(O)CF$_3$, sulfone alkyl, sulfone aryl, S(O)$_2$CH$_3$, S(O)$_2$ CF$_3$, haloalkyl, CF$_3$, N$_3$, and CN.

with the proviso that C(R$^5$)$_2$ can also be C(O), each R$^6$ is independently selected from —C(O)—, —C(S)— and —C(NR$^z$)—;

each R$^{10}$ and R$^{11}$ are independently selected from H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more substituents as defined above, for example, hydroxyaryl, aminoalkyl, and alkoxyalkyl;

each R$^{12}$ and R$^{16}$ are independently selected from hydrogen, R$^{13}$—C(O)—, R$^{13}$—C(S)—, and R'; Each R' is as defined above;

each R$^{13}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')$_2$, wherein each R' is as defined above;

R$^{14}$ and R$^{14'}$ are independently selected from halogen (F, Cl, Br, I), CF$_3$, hydroxy, alkoxy (C$_{1-6}$), aryl, 5-membered heteroaryl, lower alkyl (C$_{1-6}$) or halo substituted aryl, aryl or halo substituted 5-membered heteroaryl, cyano, alkynyl (C$_{2-6}$), alkoxyalkyl (C$_{3-6}$), alkoxycarbonylalkyl, alkyl, arylalkoxycarbonyl, carboxy, haloalkyl, heterocyclylalkyl, hydroxyalkyl; and R$^{15}$ and R$^{15'}$ are independently selected from hydrogen, alkoxy (C$_{2-6}$), alkoxyalkyl (C$_{3-6}$), alkoxycarbonyl, carbonylalkyl, carbonyl aryl, alkyl, heterocyclylalkyl, hydroxyalkyl (C$_{2-6}$), and pharmaceutically acceptable salts and prodrugs thereof, wherein the compounds can be in the form of the R- or S-configuration, or a mixture thereof, including a racemic or diastereomeric mixture thereof.

The compounds described herein can be in the form of the R- or S-configuration, or a mixture thereof, including a racemic or diastereomeric mixture thereof.

Representative compounds include the following:
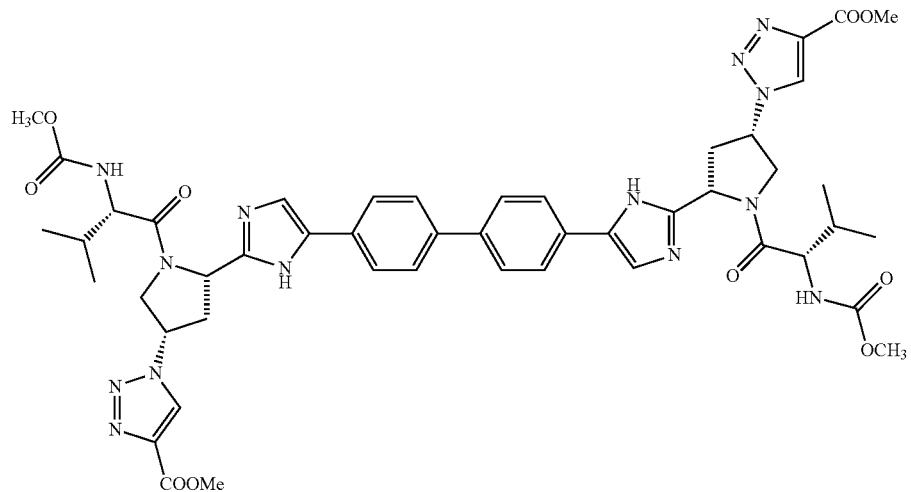
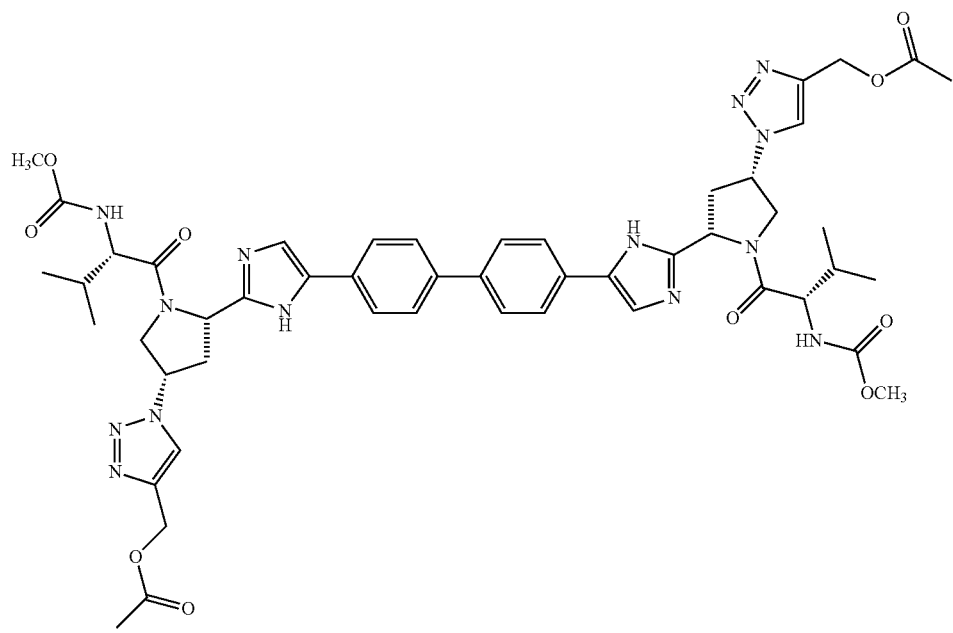
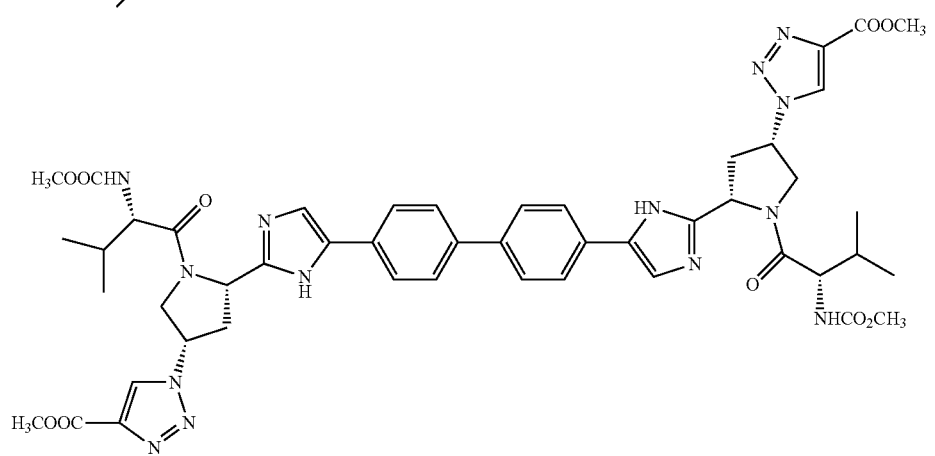

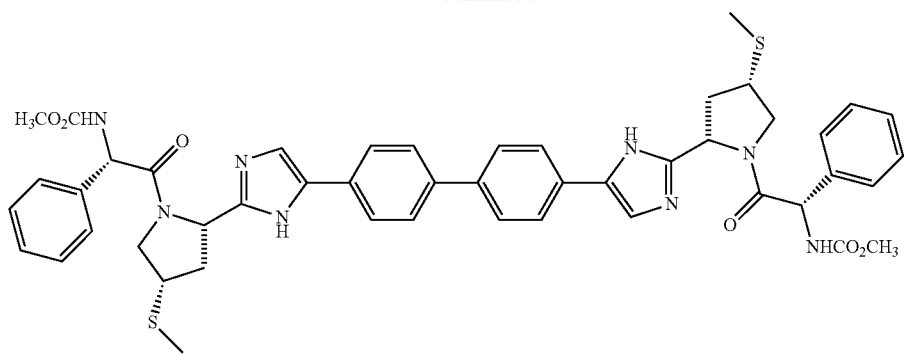
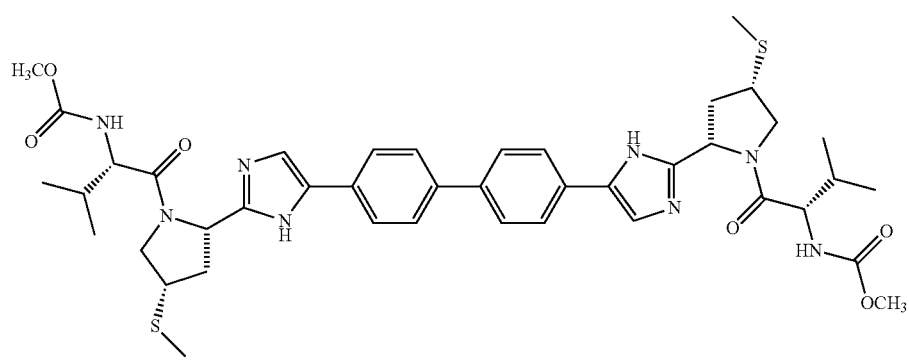
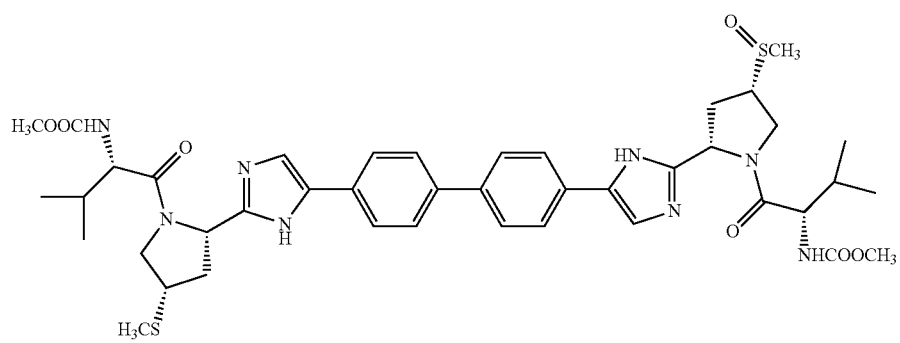
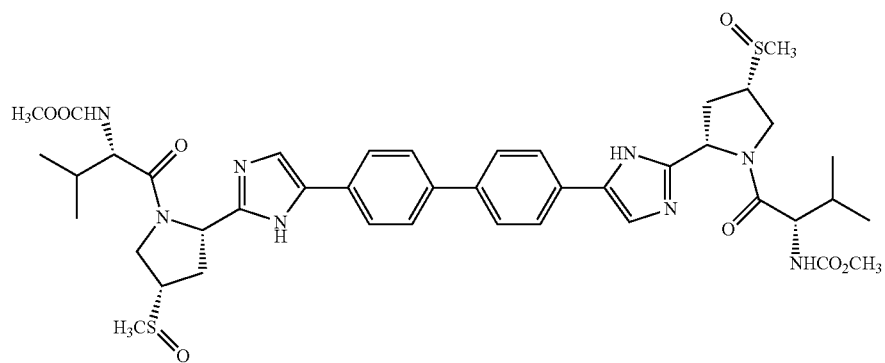

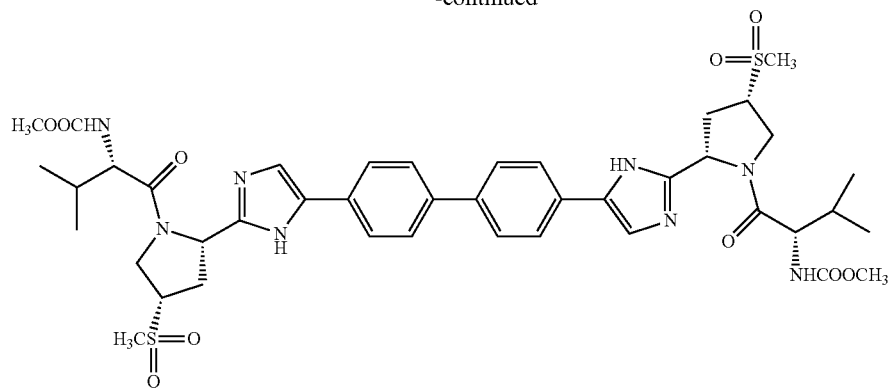
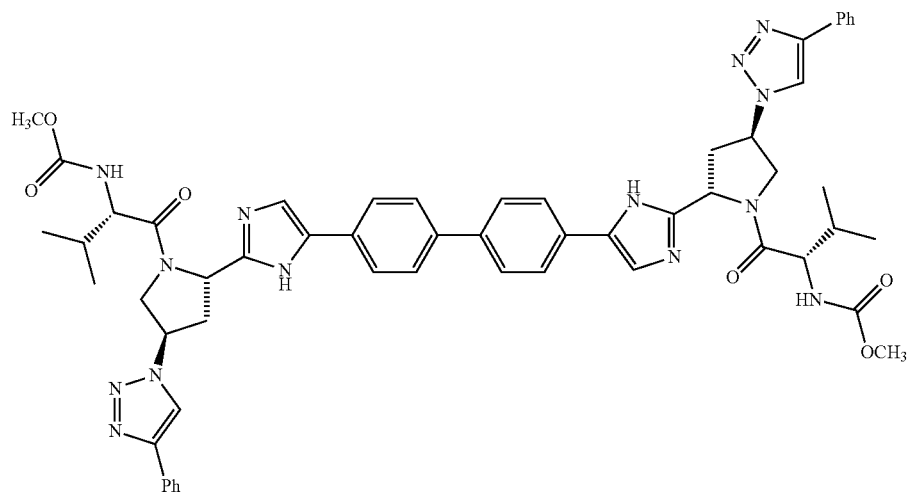
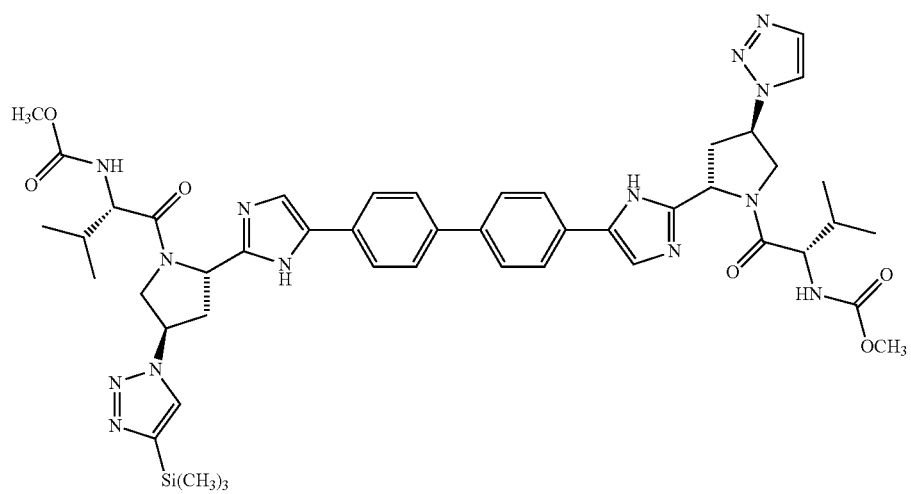

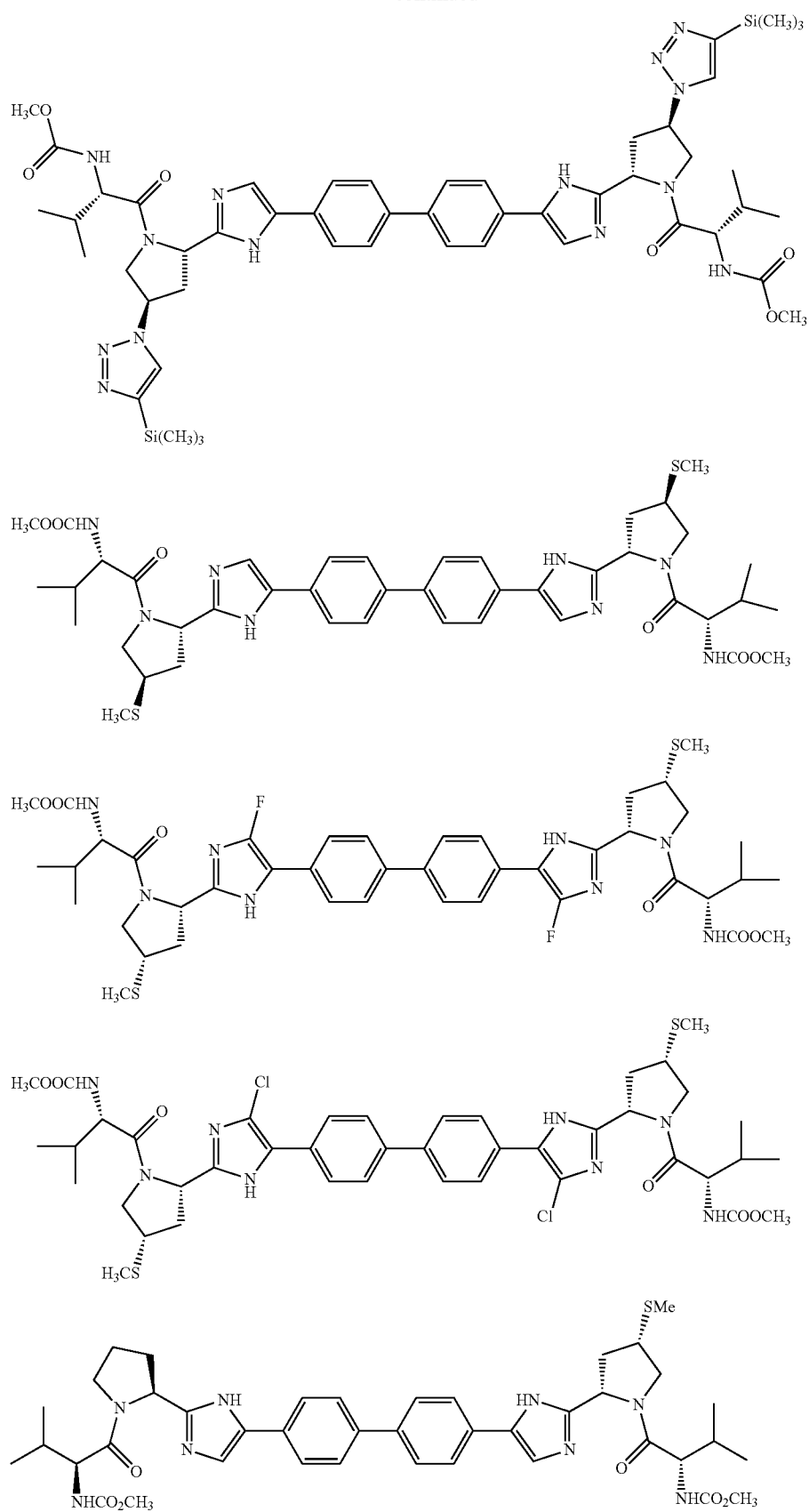

-continued

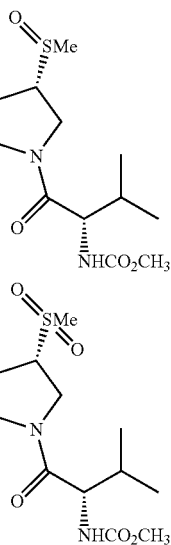

III. Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Methods of Treatment

Hosts, including but not limited to humans, infected with HCV or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

VI. Combination or Alternation Therapy

In one embodiment, the compounds of the invention can be employed together with at least one other antiviral agent, selected from polymerase inhibitors, IMPDH inhibitors, protease inhibitors, and immune-based therapeutic agents.

For example, when used to treat or prevent HCV infection, the active compound or its prodrug or pharmaceutically acceptable salt can be administered in combination or alternation with another anti-HCV including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

Table of Anti-Hepatitis C Compounds in Current Clinical Development

| Drug Name | Drug Category | Pharmaceutical Company |
| --- | --- | --- |
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/ LY 570310 | Protease Inhibitor | Vertex/Eli Lilly |
| ISIS 14803 | Antisense | Isis Pharmaceutical/ Elan |
| IDN-6556 | Caspase inhibitor | Idun Pharmaceuticals, Inc. http://www.idun.com |

-continued

| Drug Name | Drug Category | Pharmaceutical Company |
|---|---|---|
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wye |
| CH-6 | Serine Protease | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monclonal Antibody | XTL |
| IC41 | Therapeutic Vaccine | Intercell |
| Medusa Interferon | Longer acting interferon | Flamel Technologies |
| E-1 | Therapeutic Vaccine | Innogenetics |
| Multiferon | Long Acting Interferon | Viragen |
| BILN 2061 | Serine Protease | Boehringer-Ingelheim |
| Interferon beta-1a (REBIF) | Interferon | Ares-Serono |

VIII. Pharmaceutical Compositions

Hosts, including but not limited to humans, infected with HCV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 300 mg, preferably 70 to 140 mg of active ingredient per unit dosage form. An oral dosage of 5-300 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

CAN acetonitrile
aq aqueous
CDI carbonyldiimidazole
DIPEA diisopropyl ethyl amine (Hünig's base)
DMF N,N-dimethylformamide
DMSO dimethylsulfoxide
EDC 1-ethyl-3-(3-dimethyllaminopropyl)carbodiimide hydrochloride
EtOAc ethyl acetate
h hour
HOBt N-hydroxybenzotriazole
M molar
min minute
Ms mesylate
NCS N-chlorosuccinimide
NBS N-bromosuccinimide
NIS N-iodosuccinimide
Pyr pyridine
rt or RT room temperature
TBAT tetrabutylammonium triphenyldifluorosilicate
TBTU O-(Benzotriazol-1-yl)-N,N,N',N'-tetramethyluronium tetrafluoroborate
TEA triethyl amine
THF tetrahydrofuran
Ts tosylate IX. General Schemes for Preparing Active Compounds Methods for the facile preparation of active compounds are provided. The compounds disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

The various reaction schemes are summarized below.

Scheme 1. is a non-limiting example of the synthesis of active compounds of the present invention, and in particular, a synthetic approach to disubstituted imidazoles.

Scheme 2. a non-limiting example of the synthesis of active compounds of the present invention, and in particular, a synthetic approach to triazolo derivatives.

Scheme 3. a non-limiting example of the synthesis of active compounds of the present invention, and in particular, a synthetic approach to trisubstituted imidazoles Scheme 1 Synthesis of Disubstituted Imidazoles

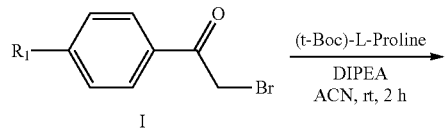

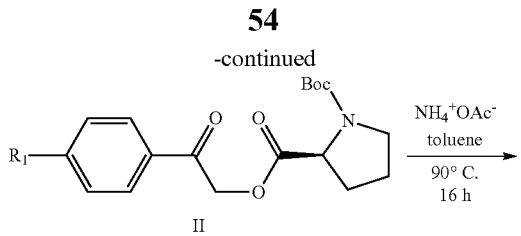

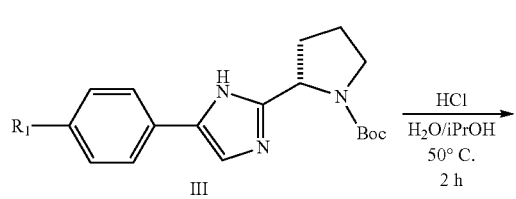

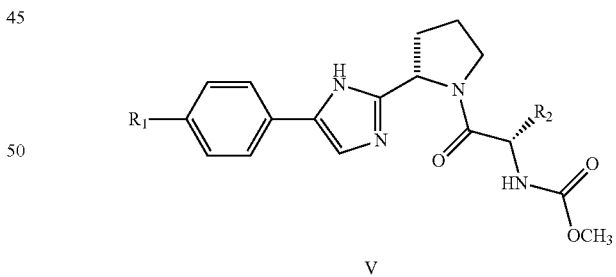

Scheme 1. A Non-Limiting Example of the Synthesis of Active Compounds of the Present Invention, and in Particular, a Synthetic Approach to Disubstituted Imidazoles The synthesis of compounds of formula V is illustrated in Scheme 1. Compounds I can be reacted with a suitable protected amino acid such as (t-Boc)-L-Proline in the presence of a non-nucleophilic base such as DIPEA, TEA, or pyr to provide compounds of formula II. Compounds II can be converted to compounds III by treatment with an ammonium source such as ammonium acetate, ammonium chloride, or ammonium formate and then deprotected, in the case of Boc protection, in presence of HCl to afford compounds IV. Finally the reaction of compound IV with an appropriately N-substituted carboxylic acid in the presence of coupling agent leads to the formation of compounds V.

-continued

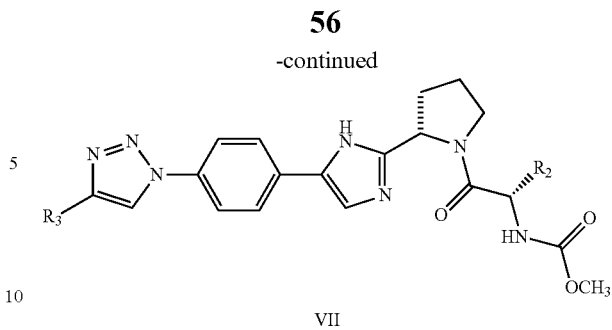

VII

Scheme 2 Synthesis of Aryl Triazolo Derivatives

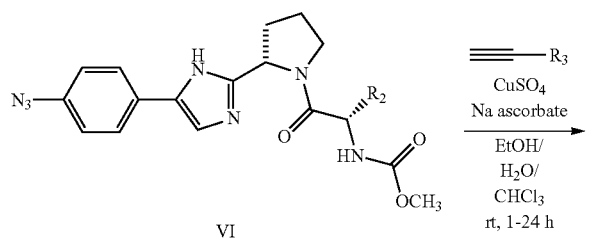

Scheme 2. A Non-Limiting Example of the Synthesis of Active Compounds of the Present Invention, and in Particular, a Synthetic Approach to Triazolo Derivatives The synthesis of compounds of formula VII is illustrated Scheme 2. Azido compounds of formula VI can be reacted with substituted alkynes to provide triazolo derivatives of formula VII.

TABLE 1

Compounds that can be prepared via Schemes 1 and 2.

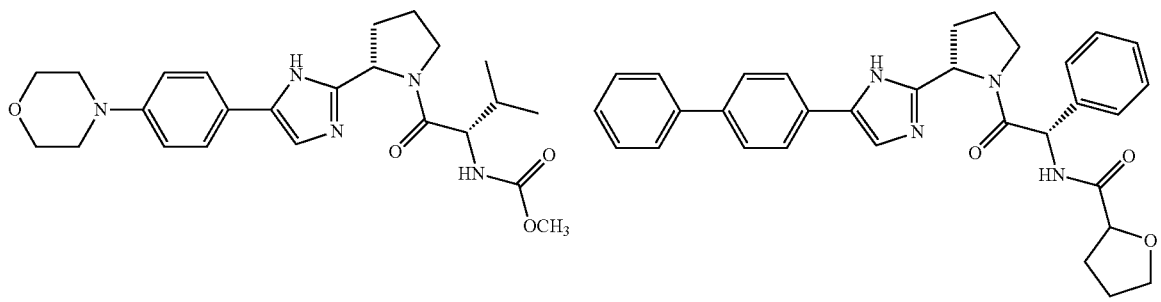

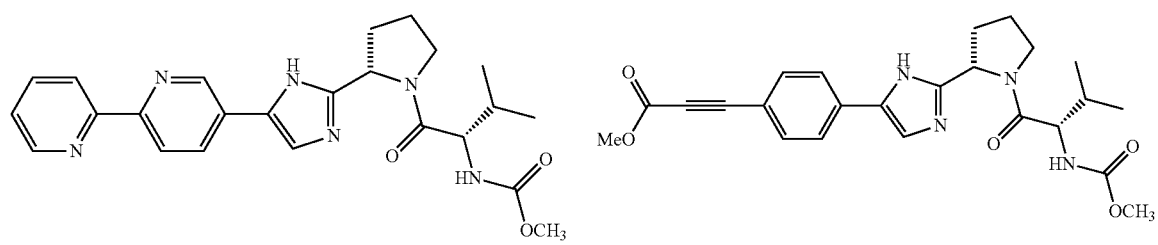

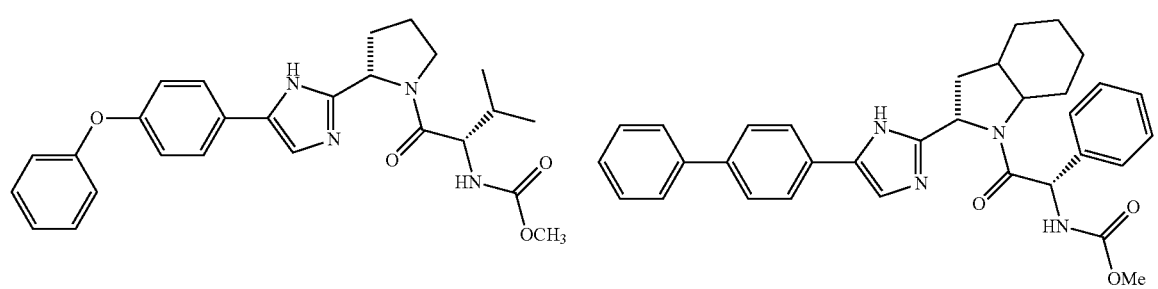

TABLE 1-continued
Compounds that can be prepared via Schemes 1 and 2.
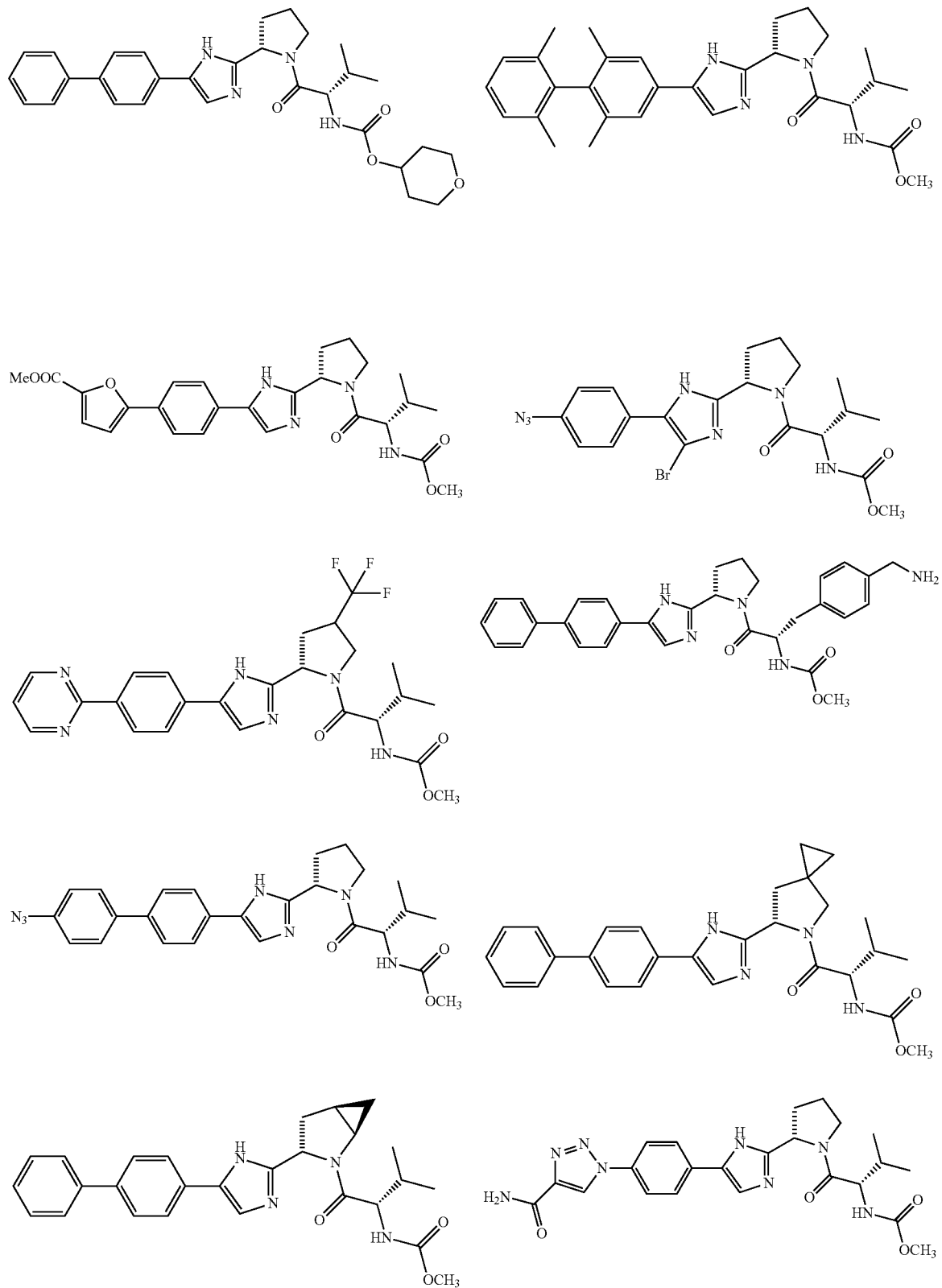

TABLE 1-continued
Compounds that can be prepared via Schemes 1 and 2.
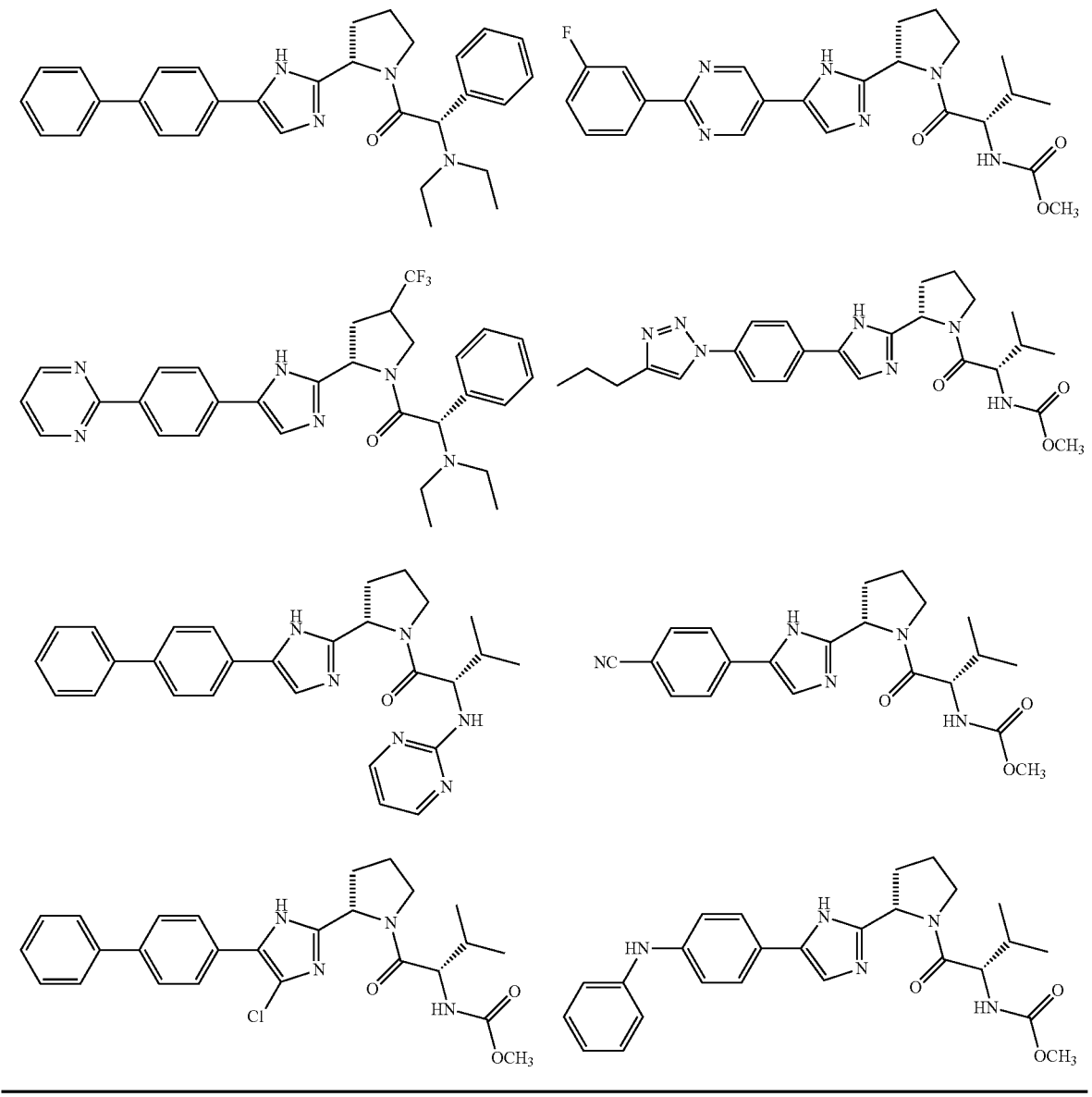
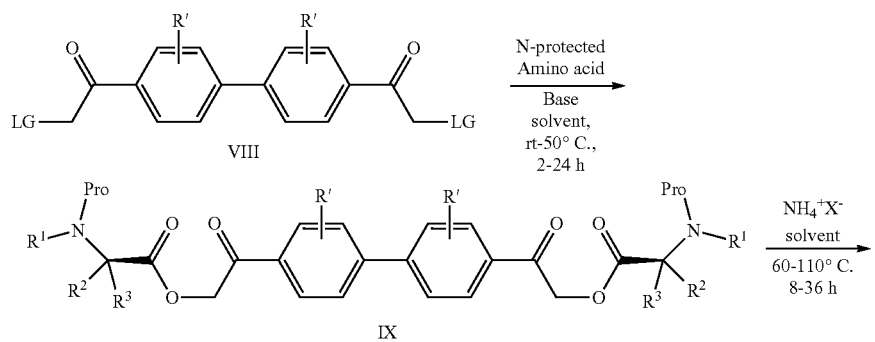
Scheme 3 Synthesis of Trisubstituted Imidazoles

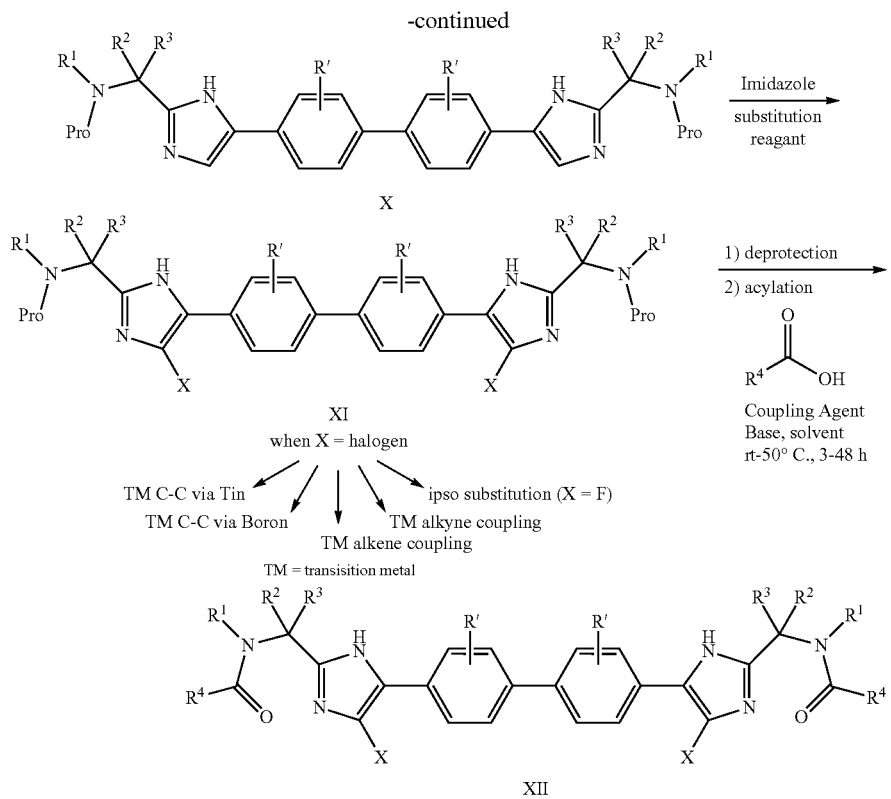

Scheme 3. A Non-Limiting Example of the Synthesis of Active Compounds of the Present Invention, and in Particular, a Synthetic Approach to Trisubstituted Imidazoles The general keto-ester IX is prepared from the bis alpha-LG keto compound VIII, in which the LG groups are suitable leaving groups such as I, Br, Cl, OMs, OTs, etc., by displacement with an appropriate cyclic or acyclic amino acid in the presence of an appropriate base, such as sodium hydride, Hünig's base, or TEA at room temperature or mild heating in solvent such as dioxane, THF, or acetonitrile (Scheme 2). Treatment IX with a source of ammonium ion such as ammonium chloride, ammonium bromide, or ammonium acetate in solvent such as xylene, DMF, THF, or toluene with heating for 8-36 h results in the formation of imidazole derivative X.

Broad substitution of the imidazole ring at the carbon or nitrogen atoms can by executed by a variety of methods known to one skilled in the art. A halogen atom can be introduced through a reagent such as NBS, NCS and NIS, and N-fluorobenzenesulfonimide. Suzuki and Stille palladium catalyzed coupling conditions can provide heteroaryl derivatives, alkenes, and alkyne derivatives. Azido or cyano groups can be introduced with reagents such as TMSCN or TMSN$_3$. Nitrogen substitution can be accomplished by acylation, alkylation, or other methods known to one skilled in the art.

Depending on the nature of the amino acid protecting group, it can be removed via strong acid or strong Lewis acid such as HCl, trifluoroacetic acid, or BBr$_3$. Hydrogenolysis or metal reduction can also provide protecting group removal.

The unmasked nitrogen atom from XI can be substituted by acylation, alkylation, or other methods known to one skilled in the art. Ultimately, compounds of type XII can be realized by acylation with an appropriately substituted carboxylic acid in the presence of standard coupling reagent such as HATU, EDCI, or PyBop in the presence of base such as Hunig's base.

The present invention is further illustrated in the following non-limiting examples. Schemes 1-3 and Examples 1-3 show preparative methods for synthesizing HCV inhibitor compounds, and Examples 4-8 show methods for their biological evaluation. It will be understood by one of ordinary skill in the art that these examples are in no way limiting and that variations of detail can be made without departing from the spirit and scope of the present invention.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee, Wis.) and EMD Chemicals Inc. (Gibbstown, N.J.). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. ¹H and ¹³C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel or via reverse-phase high performance liquid chromatography.

Example 1

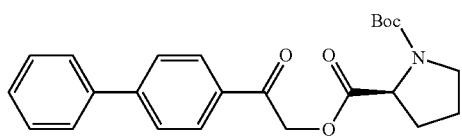

(S)-2-(2-([1,1'-biphenyl]-4-yl)-2-oxoethyl) 1-tert-butyl pyrrolidine-1,2-dicarboxylate To a stirred suspension of 2-Bromo-4'-phenylacetophenone (3 g, 10.9 mmol, 1 eq) and (tBOc)-L-Proline (2.58 g, 12 mmol, 1.1 eq) in acetonitrile (40 mL) was added DIPEA (2.08 mL, 12 mmol, 1.1 eq) under an argon atmosphere. The reaction was stirred at room temperature approximately 2 h until LC/MS suggested that all the starting material was consumed. The reaction solution was then diluted with AcOEt (250 mL) and washed with H₂O (2×100 mL). The organic layer was dried over MgSO₄, filtered and evaporated under reduced pressure. The crude compound 1 was then directly engaged into the next step.

LCMS Calcd for C₂₄H₂₇NO₅ 409.2, Observed (M-Boc) 310.1

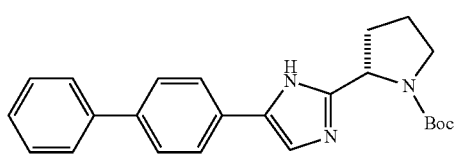

(S)-tert-butyl 2-(5-([1,1'-biphenyl]-4-yl)-1H-imidazol-2-yl)pyrrolidine-1-carboxylate A solution of 1 (4.46 g, 10.9 mmol, 1 eq) in toluene (40 mL) was charged with ammonium acetate (16.78 g, 218 mmol, 20 eq) and heated to 95° C. for 16 h under an argon atmosphere. After reaction completion, the mixture was cooled to room temperature and diluted with AcOEt (250 ml). The organic layer was washed with H₂O (2×100 mL), dried over MgSO₄, filtered and evaporated under reduced pressure. The crude product was finally purified by column chromatography (AcOEt/Hexane: 5/5) to afford compound 2 (4 g, 95%) as a brownish amorphous solid.

LCMS Calcd for C₂₄H₂₇N₃O₂ 389.2, Observed (M+1) 390.1

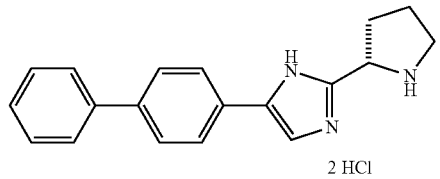

(S)-5-([1,1'-biphenyl]-4-yl)-2-(pyrrolidin-2-yl)-1H-imidazole dihydrochloride salt To a solution of 2 (2 g, 5.14 mmol, 1 eq) in iPrOH (9 mL) and H₂O (4.5 mL) is added concentrated HCl (1.6 mL, 51.4 mmol, 10 eq). The resulting solution was heated to 50° C. for approximately 2 h until LC/MS suggested that all the starting material was consumed. After evaporation of the volatiles under reduced pressure the crude compound 3 was then directly engaged into the next step.

LCMS Calcd for C₁₉H₁₉N₃ 289.2, Observed (M+1) 290.1

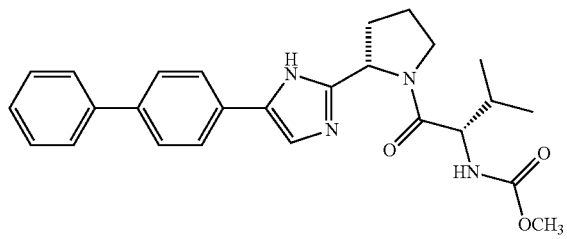 [SMILES: COC(=O)N[C@H](C(=O)N1CCC[C@H]1c1ncc(-c2ccc(-c3ccccn3)nc2)[nH]1)C(C)C]

Methyl ((S)-1-((S)-2-(5-([1,1'-biphenyl]-4-yl)-H-imidazol-2-yl)pyrrolidin-1-yl)-3-methyl-1-oxobutan-2-yl)carbamate To a solution of HOBT (55 mg, 0.36 mmol, 1.3 eq), EDC (64 mg, 0.33 mmol, 1.2 eq) and the protected amino acid (58 mg, 0.33 mmol, 1.2 eq) in acetonitrile (1.5 mL) stirred for 1 h is added 3 (0.1 g, 0.276 mmol, 1 eq). The reaction mixture was cooled to about 0° C. and DIPEA (96 µL, 0.552 mmol, 2 eq) was added dropwise. The resulting solution was then stirred for approximately 15 h at room temperature until LC/MS suggested that all the starting material was consumed. The reaction solution was then diluted with AcOEt (250 mL) and washed with H₂O (2×100 mL). The organic layer was dried over MgSO₄, filtered and evaporated under reduced pressure. The crude product was finally purified by column chromatography (DCM/MeOH: 95/5) to afford compound 4 (113 mg, 92%) as a white amorphous solid.

¹H NMR (DMSO-d₆) δ 0.75-0.88 (m, 6H), 1.80-2.01 (m, 3H), 2.05-2.15 (m, 1H) 3.24-3.35 (m, 2H), 0.49 (s, 3H), 3.71-3.79 (m, 1H), 3.95-4.03 (m, 1H), 5.03-5.05 (m, 1H), 7.27-7.77 (m, 10H), 11.77 (s, 1H). LCMS Calcd for C₂₆H₃₀N₄O₃ 446.2, Observed (M+1) 447.1

Example 2

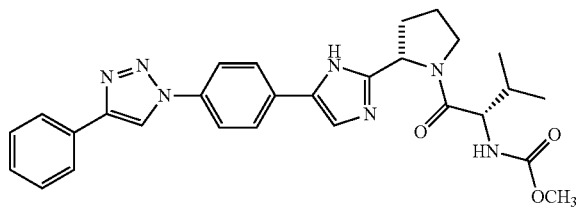

Methyl ((S)-3-methyl-1-oxo-1-((S)-2-(5-(4-(4-phenyl-H-1,2,3-triazol-1-yl)phenyl)-1H-imidazol-2-yl)pyrrolidin-1-yl)butan-2-yl)carbamate To a solution of 6 (30 mg, 0.073 mmol, 1 eq) in CHCl$_3$ (0.5 mL) and H$_2$O (0.25 mL) is added successively phenylacetylene (8 μL, 0.073 mmol, 1 eq), CuSO$_4$·5H$_2$O (18 mg, 0.073 mmol, 1 eq), Sodium acetate (14.5 mg, 0.073 mmol, 1 eq) and EtOH (0.5 mL). The resulting mixture was then stirred for approximately 2 h at room temperature until LC/MS suggested that all the starting material was consumed. After evaporation of the volatiles under reduced pressure the crude product was finally purified by column chromatography (DCM/MeOH: 95/5) to afford compound 7 (20 mg, 55%) as an amorphous solid.

$^1$H NMR (MeOD) δ 0.87-0.95 (m, 6H), 1.98-2.33 (m, 3H), 3.68 (s, 3H), 3.85-3.90 (m, 1H), 3.95-4.00 (m, 1H), 4.19-4.25 (m, 1H), 5.12-5.17 (m, 1H), 7.33-7.46 (m, 4H), 7.86-7.92 (m, 6H), 8.88-8.92 (m, 1H). LCMS Calcd for C$_{28}$H$_{31}$N$_7$O$_3$ 513.2, Observed (M+1) 514.1

Example 3

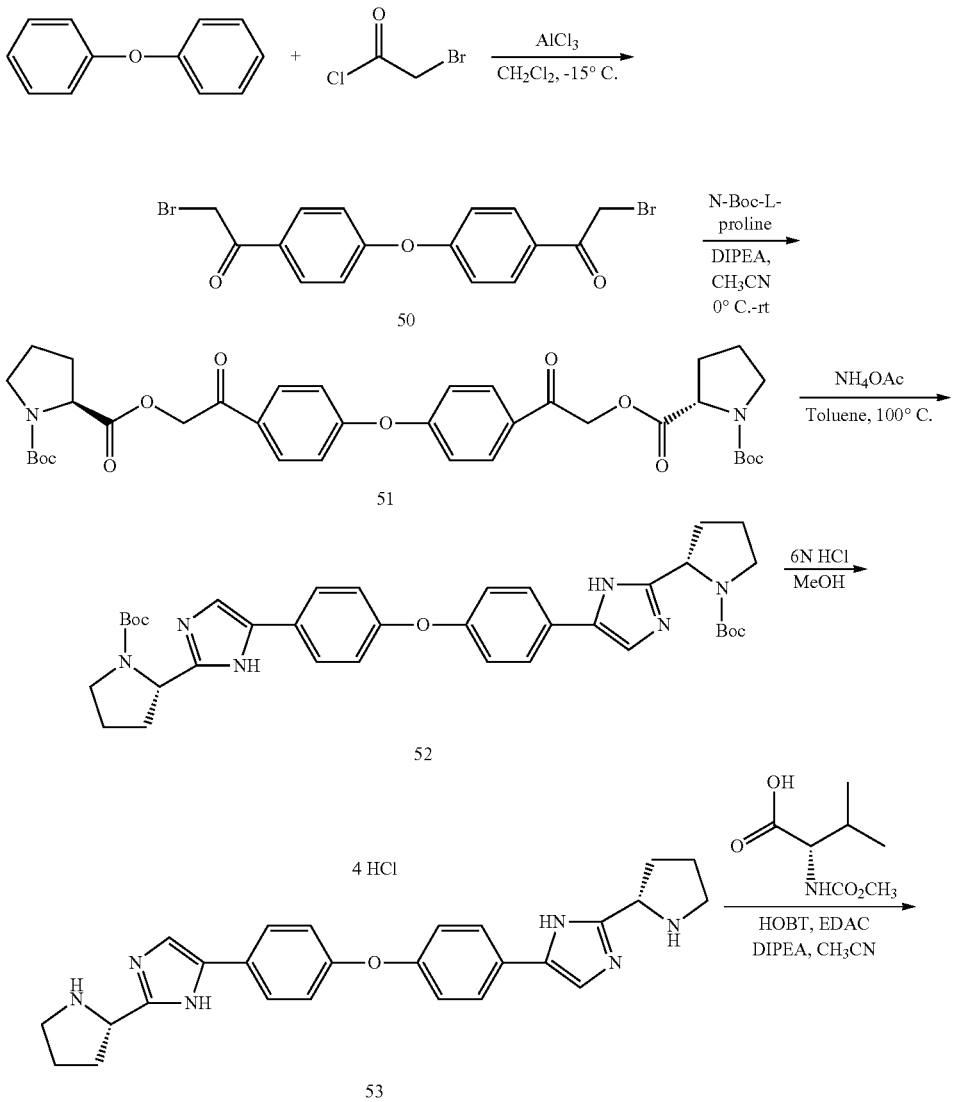

Scheme 4. Synthesis of biphenyl ether 54

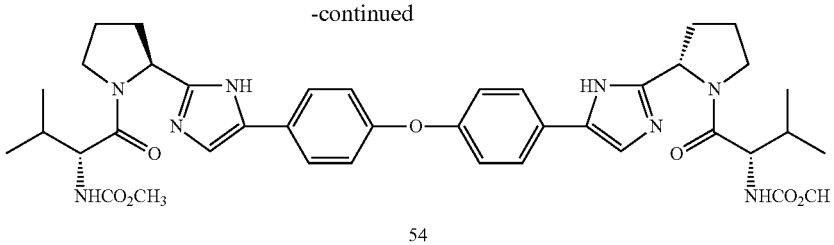

54

Preparation of 1,1'-(oxybis(4,1-phenylene))bis(2-bromoethanone), 50

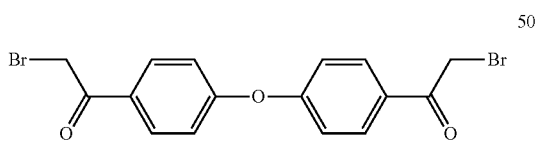 [SMILES: O=C(CBr)c1ccc(Oc2ccc(C(=O)CBr)cc2)cc1]

50

Bromoacetyl chloride (2.22 ml, 22 mmol) was added dropwise during 15 min with stirring at −15° C. to a mixture of aluminum chloride (6.0 g, 44.8 mmol) in methylene dichloride (40 ml). The reaction mixture was stirred at −15° C. for an additional 3 min. Diphenyl ether (1.87 g, 11.0 mmol) was added during 30 min with stirring at −15° C. and the reaction mixture was allowed to warm to room temperature and then stirred for 3 h. It was then poured into a mixture of concentrated hydrochloric acid and crushed ice and extracted with methylene dichloride (2×50 ml). The combined organic extracts were washed with 2% aqueous sodium hydrogen carbonate and water and dried over $Na_2SO_4$. Evaporation of the solvent under reduced pressure gave desired product 50 3.03 g (67%).

Preparation of (2S,2'S)-di-tert-butyl 2,2'-(5,5'-(oxy-bis(4,1-phenylene))bis(1H-imidazole-5,2-diyl))bis(pyrrolidine-1-carboxylate), 52

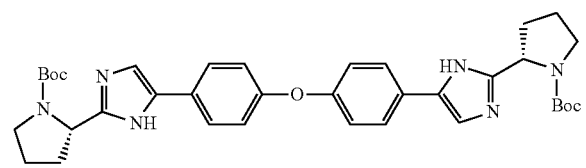

52

0.91 ml of diisopropylethylamine was added dropwise (DIPEA, 5.2 mmol) to a mixture of compound 50 (1.04 g, 2.52 mmol) and 1-(t-butoxycarbonyl)-L-proline (1.14 g, 5.3 mmol) in acetonitrile (10 ml) at 0° C. The resulting mixture was then warmed to room temperature and allowed to stir for 3 hours. The reaction was quenched with 20 ml of water and extracted with ethyl acetate (2×50 ml). The combined organic extracts was washed with saturated brine (30 ml) and dried over sodium sulfate. Evaporation of the solvent under reduced pressure gave pale yellow foam 51, which was added 4 g of ammonium acetate and 15 ml of toluene. The mixture was stirred at 100° C. overnight (~12 hours). After the reaction completed, the solvent was evaporated under reduced pressure. The residue was portioned with 60 ml of ethyl acetate and 30 ml of water. The aqueous phase was extracted with ethyl acetate (2×60 ml). The combined organic extracts were washed with brine (30 ml), dried over sodium sulfate. After removed the solvent, the residue was purified by column chromatography on silica gel (ethyl acetate/hexane=0 to 100%) to give product 52. LC-MS m/z=641 (M+1)⁺.

Preparation of (S)-5,5'-(oxybis(4,1-phenylene))bis(2-((S)-pyrrolidin-2-yl)-1H-imidazole), 53

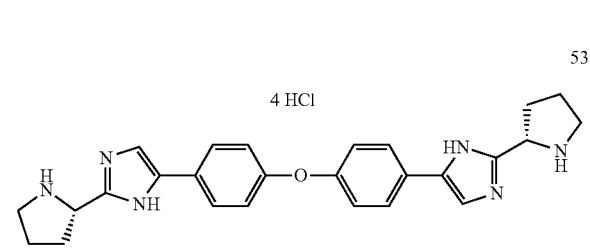 [SMILES: c1cc(-c2cnc([C@@H]3CCCN3)[nH]2)ccc1Oc1ccc(-c2cnc([C@@H]3CCCN3)[nH]2)cc1]

53

To a solution of compound 52 (330 mg, 0.515 mmol) in methanol (3 mL) was added 6N HCl (3.6 mL). The mixture was stirred at 55° C. for 5 h. After the reaction completion, the solvent was removed under reduced pressure. The residue was collected and washed with ethyl acetate/hexane (1:1, v/v) to give product 53 in 99% yield. LC-MS m/z=441 (M+1)⁺.

Preparation of dimethyl ((2S,2'S)-((2S,2'S)-2,2'-(5, 5'-(oxybis(4,1-phenylene))bis(1H-imidazole-5,2-diyl))bis(pyrrolidine-2,1-diyl))bis(3-methyl-1-oxobutane-2,1-diyl))dicarbamate, 54

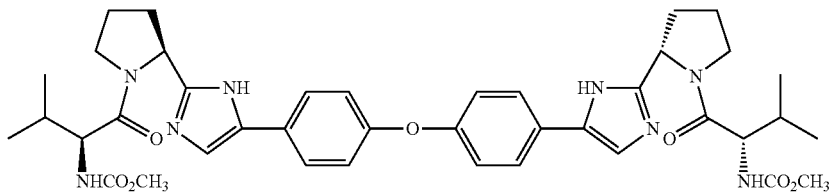

54

A mixture of N-(methoxycarbonyl)-L-valine (75.4 mg, 0.43 mmol), 68.5 mg HOBT (hydroxybenzotriazole hydrate) and 82.3 mg of 1-(dimethylaminopropyl)-3-ethylcarbodiimide hydrochloride (0.43 mmol) in 3 mL of anhydrous acetonitrile was stirred at room temperature for 1 h. The solution was added compound 53 (105.6 mg, 0.18 mmol). The mixture was cooled with ice bath and 0.14 mL of diisopropylethylamine (0.71 mmol) was added at 0° C. The solution was stirred from 0° C. to room temperature for 1 h and then overnight at room temperature. After removed the solvent, the residue was purified by column chromatography on silica gel (ethyl acetate/hexane, 50% to 100% ethyl acetate) to give 115 mg of product 54 (85% yield). LC-MS m/z=755 (M+1)$^+$. $^1$H NMR (400 MHz, CDCl$_3$) δ ppm 10.46 (m, 2H), 7.70-7.68 (m, 2H), 7.34-6.95 (m, 8H), 5.77 (m, 2H), 5.30-5.22 (m, 2H), 4.33-4.30 (m, 2H), 3.86-3.46 (m, 10H), 3.03-2.30 (m, 2H), 2.19-1.94 (m, 8H), 1.06-0.86 (m, 12H).

Example 4

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity IC$_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

Example 5

Mitochondrial Toxicity Assays in HepG2 Cells
i) Effect of Compounds on Cell Growth and Lactic Acid Production The effect on the growth of HepG2 cells can be determined by incubating cells in the presence of 0 μM, 0.1 μM, 1 μM, 10 μM and 100 μM drug. Cells (5×10$^4$ per well) can be plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number can be determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the compounds on lactic acid production, HepG2 cells from a stock culture can be diluted and plated in 12-well culture plates at 2.5×10$^4$ cells per well. Various concentrations (0 μM, 0.1 μM, 1 μM, 10 μM and 100 μM) of compound were added, and the cultures can be incubated at 37° C. in a humidified 5% CO$_2$ atmosphere for 4 days. At day 4, the number of cells in each well can be determined and the culture medium collected. The culture medium is then filtered, and the lactic acid content in the medium can be determined using a colorimetric lactic acid assay (Sigma-Aldrich). Since lactic acid product can be considered a marker for impaired mitochondrial function, elevated levels of lactic acid production detected in cells grown in the presence of test compounds would indicate a drug-induced cytotoxic effect.

ii) Effect on Compounds on Mitochondrial DNA Synthesis:

A real-time PCR assay to accurately quantify mitochondrial DNA content has been developed (see Stuyver L J, Lostia S, Adams M, Mathew J S, Pai B S, Grier J, Thamish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay can be used in all studies described in this application that determine the effect of compounds on mitochondrial DNA content. In this assay, low-passage-number HepG2 cells are seeded at 5,000 cells/well in collagen-coated 96-well plates. Test compounds are added to the medium to obtain final concentrations of 0 μM, 0.1 μM, 10 μM and 100 μM. On culture day 7, cellular nucleic acids are prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the β-actin or rRNA gene are amplified from 5 μl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3', 5'-tetrachloro-6-carboxyfluorescein-TCCTCATCGCCCTCCCATCCC-TAMRA-3' and 5'-CGTCTGTTATGTAAAGGATGCGT-3'. For exon 3 of the β-actin gene (GenBank accession number E01094) the sense, probe, and antisense primers are 5'-GCGCGGC-TACAGCTTCA-3', 5'-6-FAMCACCACGGC-CGAGCGGGATAMRA-3' and 5'-TCTCCTTAATGT-CACGCACGAT-3', respectively. The primers and probes for the rRNA gene are commercially available from Applied Biosystems. Since equal amplification efficiencies are obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample–CT for target control)–(CT for average reference test–CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

Example 6

Mitochondrial Toxicity Assays in Neuro2A Cells

To estimate the potential of the compounds of this invention to cause neuronal toxicity, mouse Neuro2A cells (American Type Culture Collection 131) were used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% ($CC_{50}$) were measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug were carried out as described above. In all experiments, ddC and AZT were used as control nucleoside analogs.

Example 7

Assay for Bone Marrow Cytotoxicity

Primary human bone marrow mononuclear cells can be obtained commercially from Cambrex Bioscience (Walkersville, Md.). CFU-GM assays can be carried out using a bilayer soft agar in the presence of 50 units/mL human recombinant granulocyte/macrophage colony-stimulating factor, while BFU-E assays use a methylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of cytotoxicity of the (-) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT can be used as a positive control. Cells can be incubated in the presence of the compound for 14-18 days at 37° C. with 5% $CO_2$, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 8

HCV Replicon Assay[1]

Huh 7 Clone B cells containing HCV Replicon RNA would be seeded in a 96-well plate at 5000 cells/well, and the compounds tested at 10 M in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds was also calculated by using the ΔCt rRNA values. 2'-C-Me-C was used as the positive control. To determine $EC_{90}$ and $IC_{50}$ values[2], ΔCt: values were first converted into fraction of starting material[3] and then were used to calculate the % inhibition.

REFERENCES

1. Stuyver L et al., Ribonucleoside analogue that blocks replication or bovine viral diarrhea and hepatitis C viruses in culture. *Antimicrob. Agents Chemother.* 2003, 47, 244-254.
2. Reed I J & Muench H, A simple method or estimating fifty percent endpoints. *Am. J. Hyg.* 27: 497, 1938.
3. Applied Biosystems Handbook Median Effective concentrations ($EC_{50}$) ranges against HCV 1b are as follow:

A=1-10 μM
B=100-999 nM
C=1-99 nM
D=<1 nM

| Structure | LC/MS (ESI, M + 1) | 1H NMR | Replicon activity[a] |
|---|---|---|---|
| 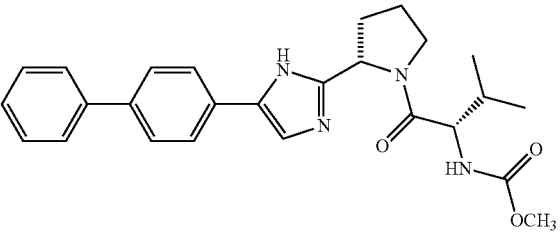  4 | Calcd for C$_{26}$H$_{31}$N$_4$O$_3$ 447.2; Observed 447.1 | $^1$H NMR (DMSO-d$_6$) δ 0.75-0.88 (m, 6H), 1.80-2.01 (m, 3H), 2.05-2.15 (m, 1H) 3.24-3.35 (m, 2H), .49 (s, 3H), 3.71-3.79 (m, 1H), 3.95-4.03 (m, 1H), 5.03-5.05 (m, 1H), 7.27-7.77 (m, 10H), 11.77 (s, 1H). | B |
| 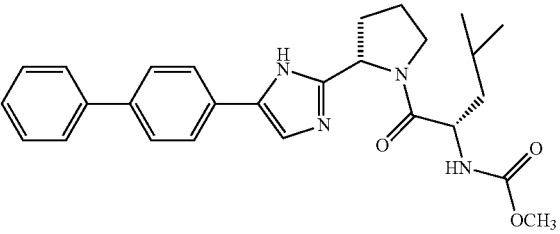  5 | Calcd for C$_{27}$H$_{33}$N$_4$O$_3$ 461.2; Observed 461.1 | $^1$H NMR (MeOD) δ 0.82-0.97 (m, 6H), 1.4.1-2.45 (m, 7H), 3.62 (m, 3H) 3.75-3.92 (m, 2H), 4.42-4.48 (m, 1H), 5.14-5.18 (m, 1H), 7.27-7.79 (m, 10H) | B |
| 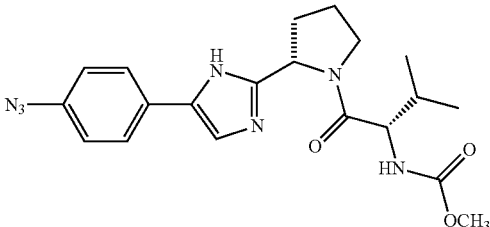  6 | Calcd for C$_{20}$H$_{26}$N$_7$O$_3$ 412.2; Observed 412.1 | $^1$H NMR (DMSO-d$_6$) δ 0.77-0.87 (m, 6H), 1.87-1.96 (m, 2H), 2.05-2.13 (m, 1H), 3.32-3.38 (m, 2H), 3.49 (s, 3H), 3.73-3.77 (m, 1H), 3.98-4.03 (m, 1H), 5.00-5.03 (m, 1H), 7.00-8.01 (m, 5H) | C |

-continued
| Structure | LC/MS (ESI, M + 1) | 1H NMR | Replicon activity[a] |
|---|---|---|---|
| 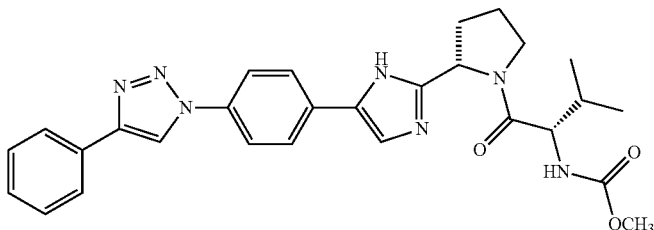<br>7 | Calcd for C$_{28}$H$_{32}$N$_7$O$_3$ 514.2; Observed 514.1 | $^1$H NMR (MeOD) δ 0.87-0.95 (m, 6H), 1.98-2.33 (m, 3H), 3.68 (s, 3H), 3.85-3.90 (m, 1H), 3.95-4.00 (m, 1H), 4.19-4.25 (m, 1H), 5.12-5.17 (m, 1H), 7.33-7.46 (m, 4H), 7.86-7.92 (m, 6H), 8.88-8.92 (m, 1H) | B |
| 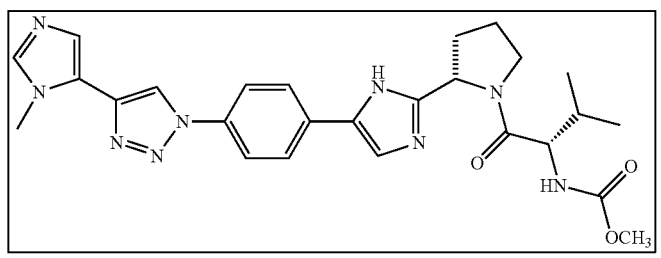<br>8 | | | B |
| 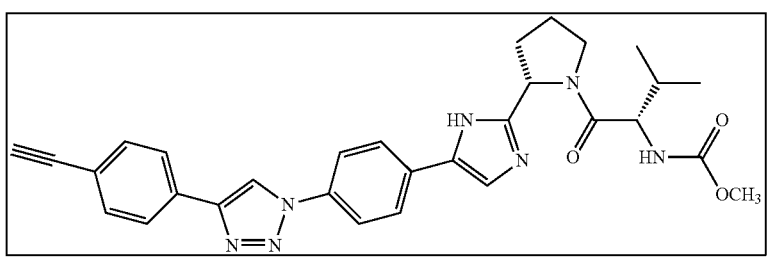<br>9 | | | C |
[a] None of the compounds were toxic in human PBM, Vero, or CEM cells at concentrations 10,000 higher than the EC$_{50}$ values for anti-HCV activity. No cytotoxicity was noted in Huh-7 cells up to 1 μM.

Example 9

A series of additional compounds was evaluated using the methods described herein. Median Effective concentrations (EC$_{50}$) ranges against HCV 1b are as follow:

A=1-10 μM
B=100-999 nM
C=1-99 nM
D=<1 nM

The data is provided below:

| Structure | Replicon EC$_{50}$ | CC$_{50}$ rRNA | Toxicities (μM) PBM | CEM | VERO |
|---|---|---|---|---|---|
| | <B | >1 μM | 53 | 13.5 | ≥100 |
| | <B | >1 μM | 53 | 13.5 | ≥100 |
| 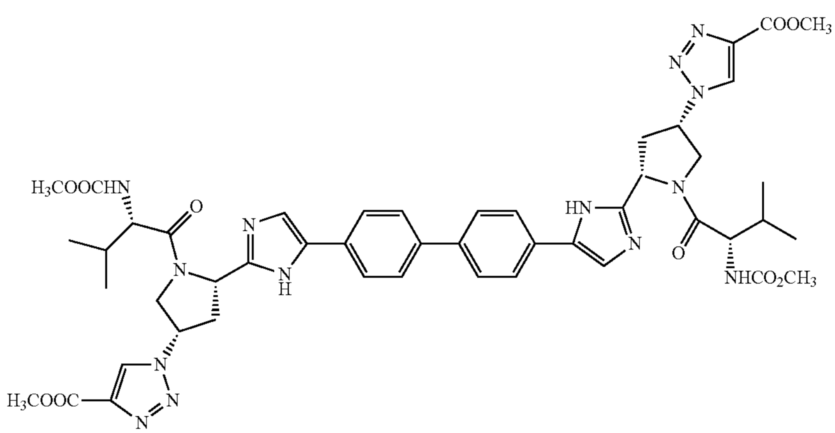 | C | >1 μM | | | |

-continued

| Structure | Replicon EC$_{50}$ | CC$_{50}$ rRNA | Toxicities (μM) PBM | CEM | VERO |
|---|---|---|---|---|---|
| (structure) | D | >1 μM | 23.9 | 1.2 | 18 |
| (structure) | D | >1 μM | 15.6 | 13.3 | 10.9 |
| (structure) | D | >33 nM | | | |
| (structure) | C | >1 μM | | | |

-continued

| Structure | Replicon EC$_{50}$ | CC$_{50}$ rRNA | Toxicities (μM) PBM | CEM | VERO |
|---|---|---|---|---|---|
| (structure) | D | >1 μM | | | |
| (structure) | C | >1 μM | >100 | >100 | >100 |
| (structure) | C | >1 μM | 3 | 16.2 | >100 |

| Structure | Replicon EC$_{50}$ | CC$_{50}$ rRNA | Toxicities (μM) PBM | CEM | VERO |
|---|---|---|---|---|---|
| (structure with Si(CH$_3$)$_3$ triazole groups) | C | >1 μM | >100 | 25.2 | >100 |
| (structure with SCH$_3$ groups) | D | >1 μM | | | |
Example 10
Metabolic Study of NS5A Inhibitors Compound A and Compound B in Human Liver Microsomes
Purpose
To identify the metabolites of Compound A and Compound B in Human Liver Microsomes.
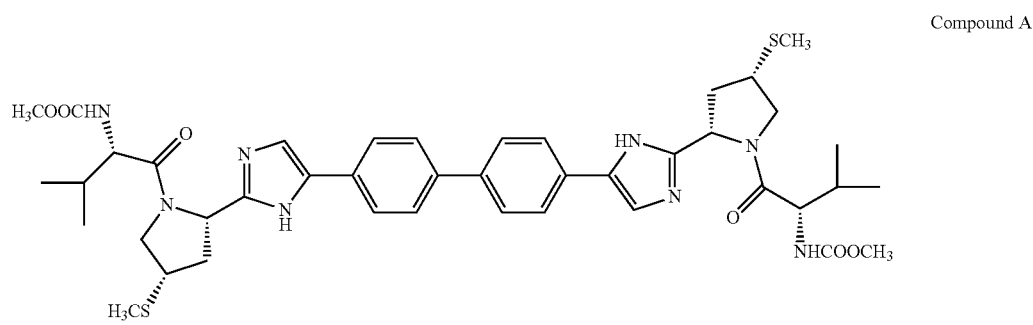
Compound A
Exact Mass: 830.4

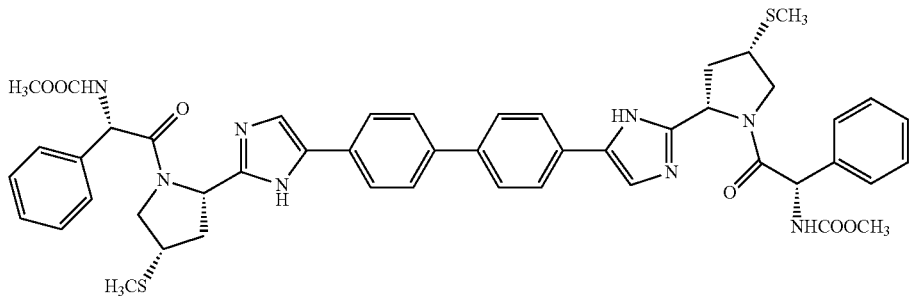

Compound B

Exact Mass: 898.3

Chemicals

Methanol and acetonitrile were purchased from (Fisher Scientific)

Formic acid was purchased from ACROS Organics.

Water was purified and deionized.

Instrumentation

The HPLC system was an Ultimate 3000 modular LC system consisting of two ternary pump, vacuum degasser, thermostated autosampler, and thermostated column compartment (Dionex Corporation; Sunnyvale, Calif.). A TSQ Quantum Ultra triple quadrupole mass spectrometer (Thermo Scientific, Waltham, Mass., USA.) was used for detection. Thermo Xcalibur software version 2.0 was used to operate HPLC, the mass spectrometer and to perform data analyses.

Method Summary & Results

Compounds (1 µM final concentration) were incubated with human liver microsomes in potassium phosphate buffer. The microsomal protein concentration in the assay was 1 mg/mL and the final percent DMSO was less than 0.2%. Reaction was started by the addition of NADPH and stopped at 60 min by 200 µL of 80% ice cold MeOH (containing 100 nM of the internal standard RS-1174). The samples were qualitatively and quantitatively analyzed by LC-MS/MS.

Gradient separation was performed on a Hypersil GOLD column (100×1.0 mm) with a 3 µm particle size (Thermo Electron, Waltham, Mass.). The mobile phase A consisted of water containing 0.1% formic acid and B consisted of acetonitrile. Mobile phase B was increased from 15% to 100% in 8 min, and kept at 100% for 2 min. The flow rate was maintained at 50 µL/min and a 25 µL injection volume was used. The autosampler was maintained at 4° C., and the column was maintained at 30° C.

The first 3.0 min of the analysis was diverted to waste. The mass spectrometer was operated in negative ionization mode with a spray voltage of 3.0 kV, sheath gas at 50 (arbitrary units), ion sweep gas at 0.2 (arbitrary units), auxiliary gas at 5 (arbitrary units), and a capillary temperature of 300° C. The collision cell pressure was maintained at 1.5 mTorr. The precursor and product ion transitions were listed in the following Table.

| Exact mass | Precursor ions (m/z) | Product ions (m/z) |
|---|---|---|
| 816.4 | 815.4 | 783.4 |
| 832.3 | 831.4 | 799.4 |
| 834.3 | 833.3 | 801.3 |
| 846.4 | 845.4 | 813.4 |
| 847.4 | 846.4 | 814.4 |
| 848.3 | 847.3 | 815.3 |
| 850.3 | 849.3 | 817.3 |
| 862.4 | 861.4 | 829.4 |
| 864.3 | 863.3 | 831.3 |
| 866.3 | 865.3 | 833.3 |
| 878.4 | 877.4 | 845.4 |
| 880.3 | 879.3 | 847.3 |
| 882.3 | 851.3 | 849.3 |
| 884.3 | 883.3 | 851.3 |
| 900.3 | 899.3 | 867.3 |
| 902.3 | 901.3 | 869.3 |
| 914.3 | 913.3 | 881.3 |
| 915.3 | 914.3 | 882.3 |
| 916.3 | 915.4 | 883.4 |
| 918.3 | 917.3 | 885.3 |
| 930.3 | 929.3 | 897.3 |
| 932.3 | 931.3 | 899.3 |
| 934.3 | 933.3 | 901.3 |
| 946.3 | 945.3 | 913.3 |

Results
The following metabolites are examined for Compound A
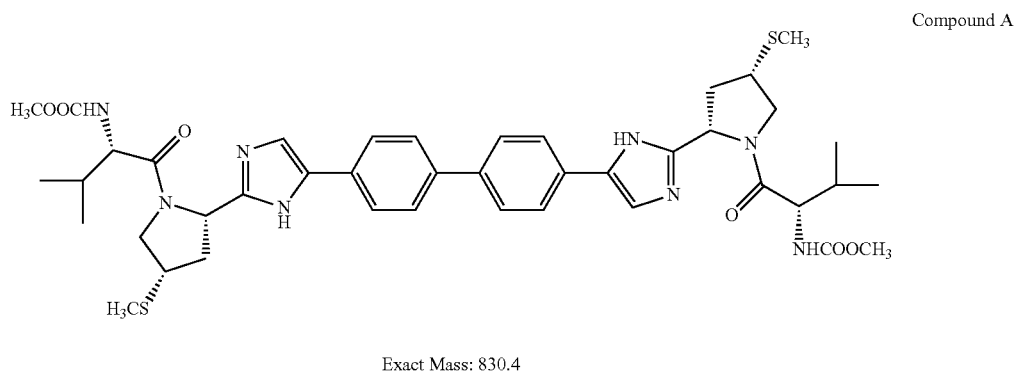
Compound A
Exact Mass: 830.4
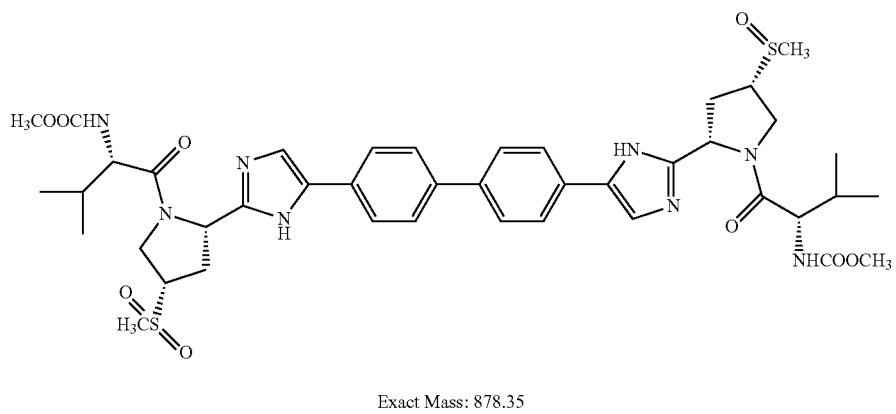
Exact Mass: 878.35
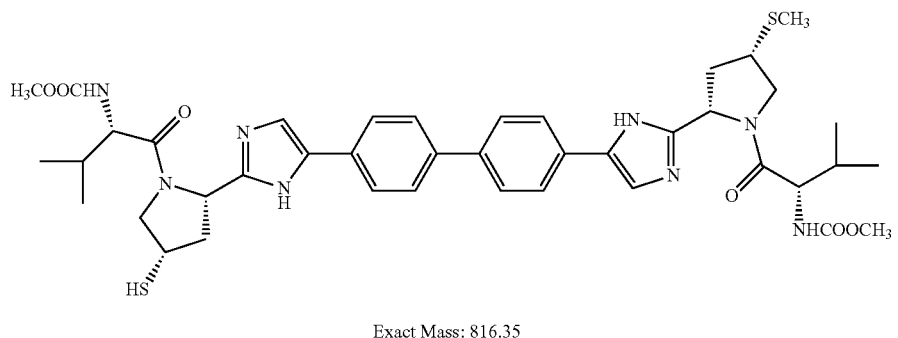
Exact Mass: 816.35
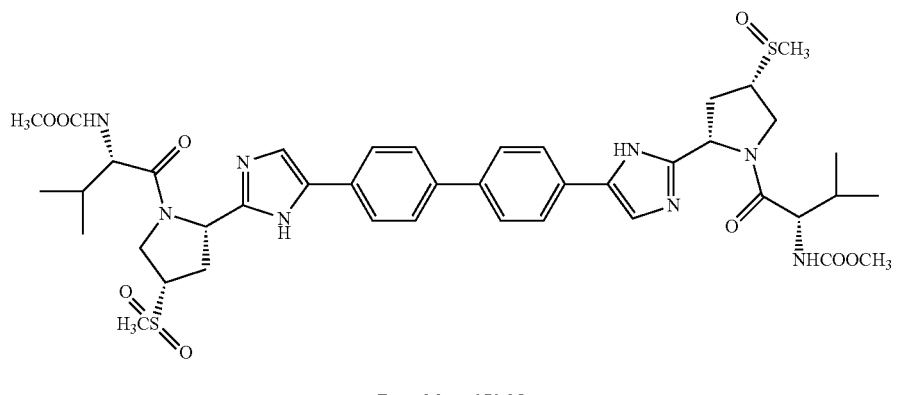
Exact Mass: 878.35

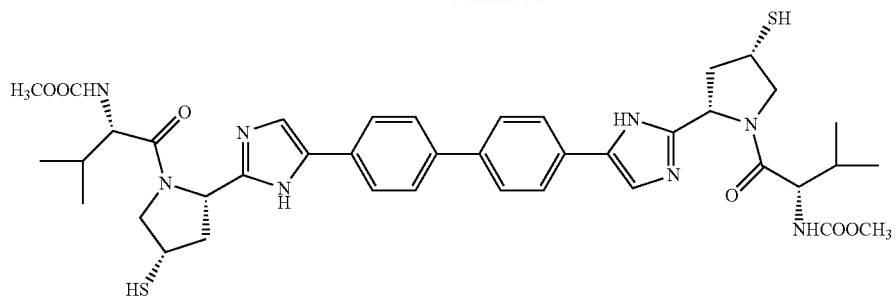
Exact Mass: 802.33
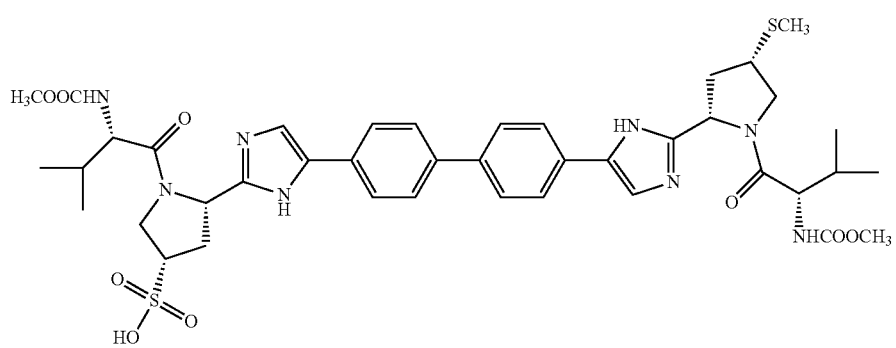
Exact Mass: 864.33
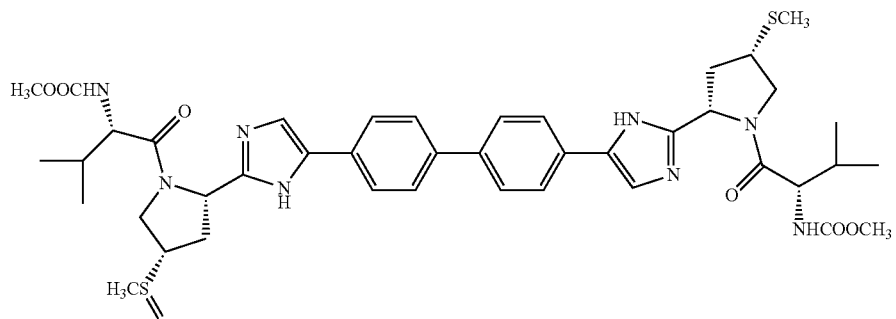
Exact Mass: 846.36
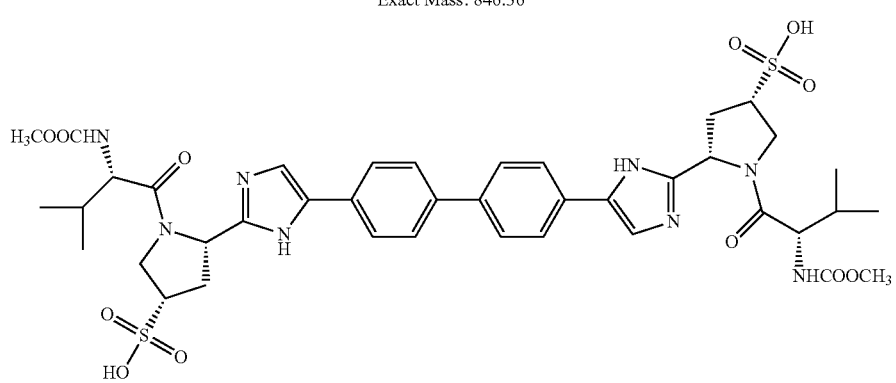
Exact Mass: 898.30

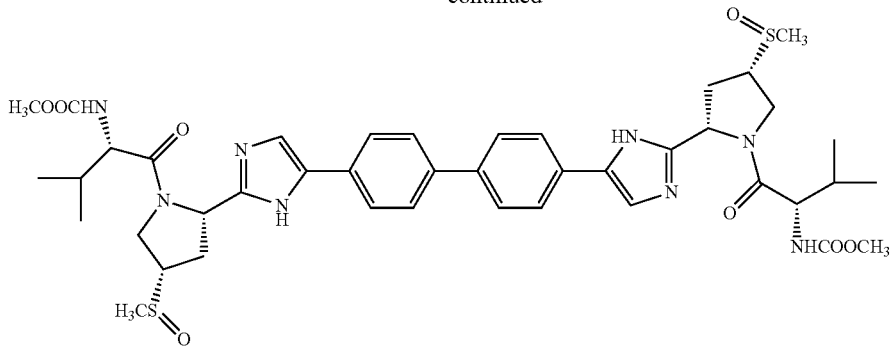
Exact Mass: 862.35
other combinations of -14, +16, and +17 are possible
The following metabolites are examined for Compound B
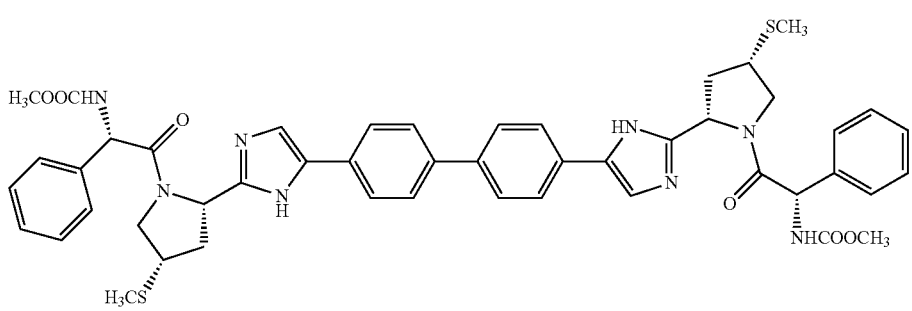
Compound B
Exact Mass: 898.3
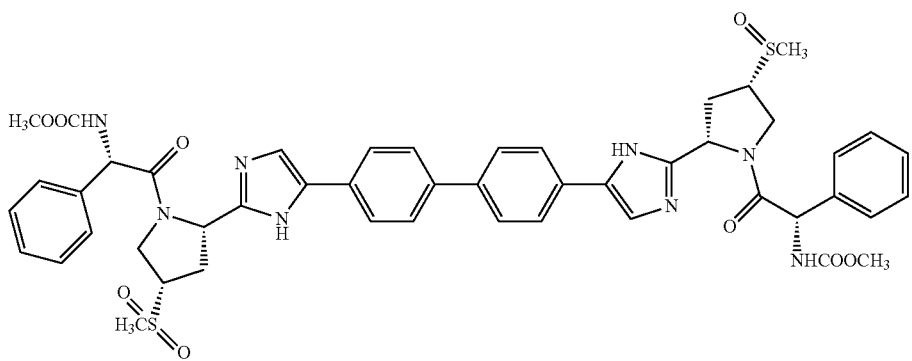
Exact Mass: 946.31
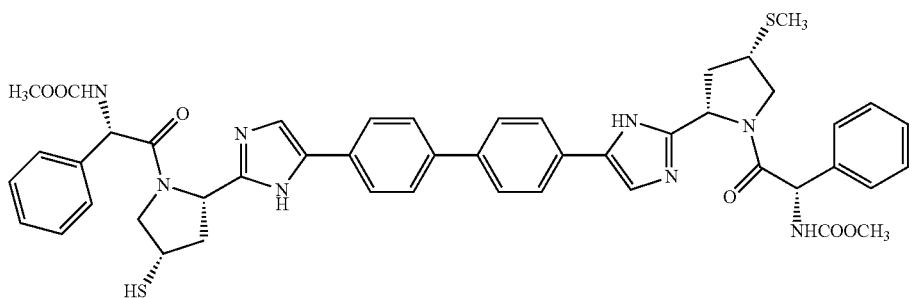
Exact Mass: 884.31

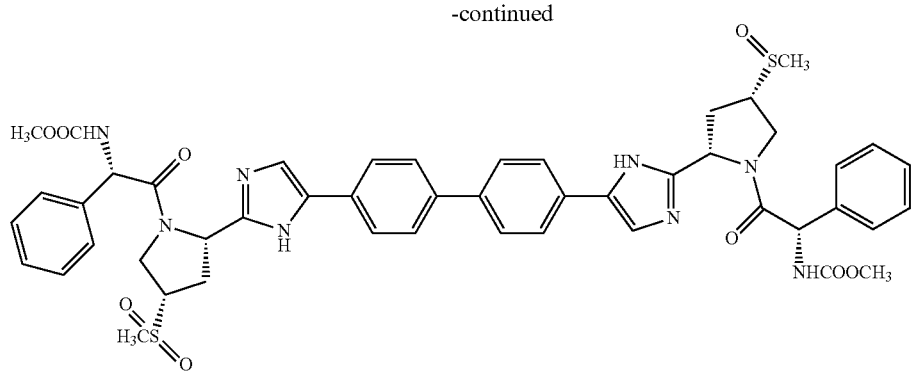
Exact Mass: 946.31
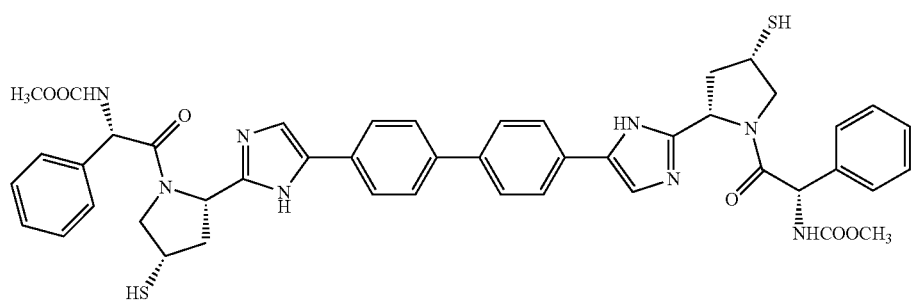
Exact Mass: 870.30
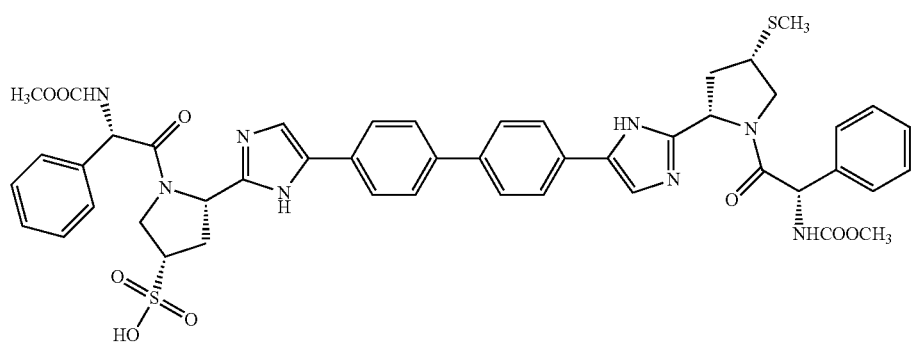
Exact Mass: 932.30
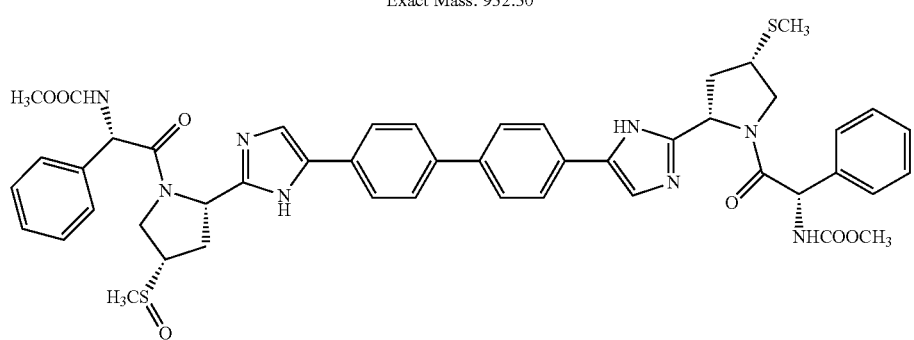
Exact Mass: 914.32

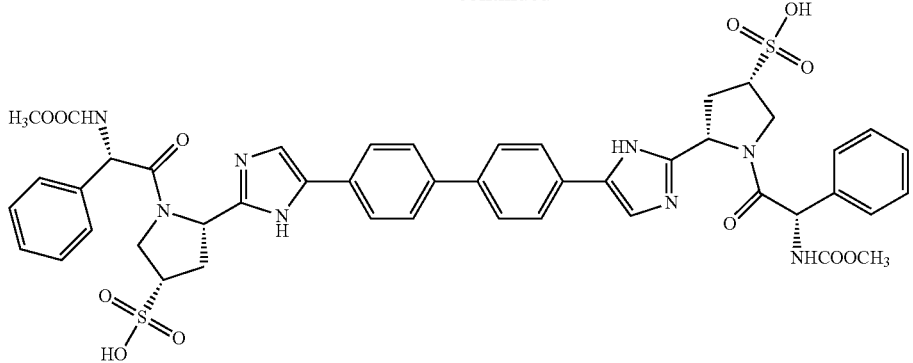

Exact Mass: 966.27

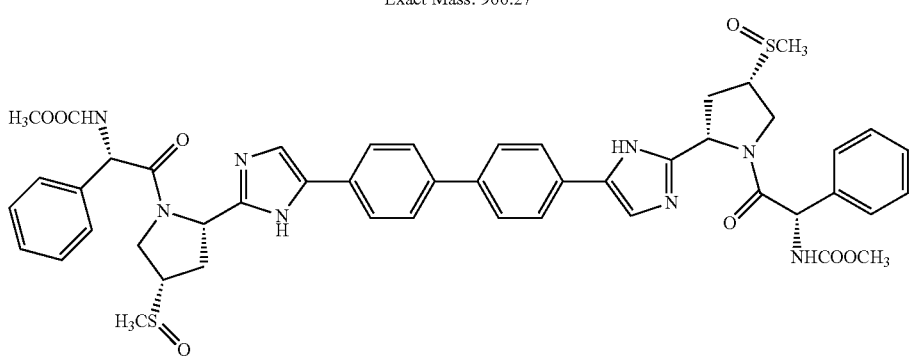

Exact Mass: 930.32 other combinations of -14, +16, and +17 are possible

The concentration of metabolites of Compound A and Compound B identified in HLM samples at 1 hr (before adjusting the data)

| Potential metabolites of Compound A | Conc. (nM) | Retention time (min) | Potential metabolites of Compound B | Conc. (nM) | Retention time (min) |
| --- | --- | --- | --- | --- | --- |
| 832.3 | 55.1 | 11.17 | 884.3 | 0.4 | 11.21 |
| 834.3-1 | 3.4 | 11.17 | 900.3 | 102.1 | 11.89 |
| 834.3-2 | 2.0 | 11.80 | 902.3 | 7.2 | 11.89 |
| 846.4 | 309.9 | 10.62 | 914.3 | 316.6 | 11.22 |
| 847.4 | 172.4 | 10.62 | 915.3 | 184.8 | 11.23 |
| 848.3 | 85.0 | 10.61 | 916.3 | 102.4 | 11.23 |
| 850.3 | 32.1 | 10.78 | 918.3 | 62.7 | 11.39 |
| 862.4 | 81.1 | 10.00 | 930.3-1 | 96.7 | 10.57 |
| 864.3 | 14.4 | 10.03 | 930.3-2 | 15.3 | 11.48 |
| 866.3 | 22.6 | 10.12 | 932.3 | 32.1 | 10.51 |
| 878.4 | 18.0 | 11.09 | 934.3 | 38.0 | 10.66 |
| 880.3 | 3.9 | 11.06 | Compound B | 323.6 | 11.87 |
| 882.3 | 2.9 | 11.17 | | | |
| Compound A | 174.1 | 11.18 | | | |

*The highlighted metabolites may be the isotopic constitute of the metabolites with molecular weight of [M-1] or [M-2], or contain the isotopic distribution.

The concentration of metabolites of Compound A and Compound B identified in HLM samples at 1 hr (after adjusting the data)

| Potential metabolites of Compound A | Conc. (nM) | Retention time (min) | Potential metabolites of Compound B | Conc. (nM) | Retention time (min) |
| --- | --- | --- | --- | --- | --- |
| 832.3 | 55.1 | 11.17 | 884.3 | 0.4 | 11.21 |
| 834.3 | 2.0 | 11.80 | 900.3 | 102.1 | 11.89 |
| 846.4 | 309.9 | 10.62 | 914.3 | 316.6 | 11.22 |
| 848.3 | 42.5 | 10.61 | 916.3 | 52.1 | 11.23 |
| 850.3 | 32.1 | 10.78 | 918.3 | 62.7 | 11.39 |
| 862.4 | 81.1 | 10.00 | 930.3-1 | 96.7 | 10.57 |
| 864.3 | 4.0 | 10.03 | 930.3-2 | 15.3 | 11.48 |
| 866.3 | 22.6 | 10.12 | 932.3 | 18.8 | 10.51 |
| 878.4 | 18.0 | 11.09 | 934.3 | 38.0 | 10.66 |
| 880.3 | 1.3 | 11.06 | Compound B | 323.6 | 11.87 |
| 882.3 | 2.9 | 11.17 | | | |
| Compound A | 174.1 | 11.18 | | | |

CONCLUSION

According to the data above, the main metabolites of Compound A incubated in human liver microsome were the ones with MW=832.3 (—CH$_2$+O), MW=846.4 (+O), and MW=862.4 (+O+O). The main metabolites of Compound B incubated in human liver microsome were the ones with MW=900.3 (—CH$_2$+O), MW=914.3 (+O), and MW=930.3 (+O+O).

The concentrations of metabolites were quantified based on the calibration curves generated from every substrate. The linear ranges were from 50 nM to 1 µM. The concentrations were estimated for those metabolites with concentrations below 50 nM.

Example 11

Identification of Two Metabolites for Compound A after Incubation in Human Liver Microsomes Purpose To identify the metabolites of Compound A in Human Liver Microsomes using standards and LC/MS.

LC/MS results for a mixture of Compound A and two standards are shown in FIG. 1.

From the chromatogram of the mixture of Compound A that was incubated in human liver microsomes (HLM) with three standards, the metabolite with exact mass=846.4 is consistent with Compound A monosulfoxide, and the metabolite with the exact mass=862.4 is consistent with Compound A bis sulfoxide. No disulfone was detected in Compound A HLM samples.

The present invention is not to be limited in scope by the specific embodiments described herein. Indeed, various modifications of the invention in addition to those described will become apparent to those skilled in the art from the foregoing description and accompanying FIGURES. Such modifications are intended to fall within the scope of the appended claims.

Various publications are cited herein, the disclosures of which are incorporated by reference in their entireties.

We claim:

1. A compound having the formula:

[chemical structure]

wherein:
$R^3$ is

[chemical structure]

each m is independently 0, 1, or 2;
n is 0, 1, 2, or 3,
each s is independently 0, 1, 2, or 3, with the proviso that at least one s is 1;
each X is, independently, O, S, S(O), $SO_2$, $CH_2$, $CHR^5$, or $C(R^5)_2$; provided that when m is 0, X is $CH_2$, $CHR^5$, or $C(R^5)_2$;
each $R^5$ is independently selected from the group consisting of thioalkyl, thioaryl, $SCF_3$, sulfoxide alkyl, sulfoxide aryl, $S(O)CH_3$, $S(O)CF_3$, sulfone alkyl, sulfone aryl, $S(O)_2CH_3$, and $S(O)_2CF_3$ with the proviso that $—C(R^5)_2$ can be $—C(O)$,
each R' is, independently, H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, arylalkyl, or if two R' reside on the same nitrogen atom, they can come together to form a $C_{3-6}$ alkyl ring containing none or one heteroatom independently selected from the group consisting of N, O and S; wherein the R' groups can be substituted with one or more hydroxyalkyl, aminoalkyl, and alkoxyalkyl substituents;

with the proviso that $C(R^5)_2$ can also be $C(=O)$,
each $R^6$ is, independently, $—C(O)—$, $—C(S)—$ or $—C(NR^z)—$;
each $R^{10}$ and $R^{11}$ are independently selected from the group consisting of H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more hydroxyaryl, aminoalkyl, or alkoxyalkyl substituents;
each $R^{12}$ and $R^{16}$ are independently hydrogen, $R^{13}—C(O)—$, $R^{13}—C(S)—$, or R'; each R' is as defined above;
each $R^{13}$ is, independently, alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, or $—N(R')_2$, wherein each R' is as defined above;
$R^{14}$ and $R^{14'}$ are, independently, H, halogen, hydroxy, $C_{1-6}$ alkoxy, aryl, 5-membered heteroaryl, $C_{1-6}$ alkyl or halo substituted aryl, aryl or halo substituted 5-membered heteroaryl, cyano, $C_{2-6}$ alkynyl, $C_{3-6}$ alkoxyalkyl, alkoxycarbonylalkyl, heterocyclylalkyl, or hydroxyalkyl; and
$R^{15}$ and $R^{15'}$ are, independently, hydrogen, $C_{2-6}$ alkoxy, $C_{3-6}$ alkoxyalkyl, alkoxycarbonyl, carbonylalkyl, carbonyl aryl, $C_{1-6}$ alkyl, heterocyclylalkyl, or $C_{2-6}$ hydroxyalkyl,
Z is $C_{1-6}$ alkyl, alkenyl, heterocyclyl, aryl, heteroaryl, halo, $—OR'$, $—NR'R''$, $—CF_3$, $—CN$, $—NO_2$, $—C_2R'$, $—SR'$, $—N_3$, $—C(=O)NR'R''$, $—NR'C(=O)$ $R''$, $—C(=O)R'$, $—C(=O)OR'$, $—OC(=O)R'$, $—OC(=O)NR'R''$, $—NR'C(=O)O$ $R''$, $—SO_2R'$, $—SO_2NR'R''$, or $—NR'SO_2R''$, where R' and R" are individually hydrogen, $C_{1-6}$ alkyl, cycloalkyl, heterocyclyl, aryl, or arylalkyl, and
j is an integer of from 0 to 3,
and pharmaceutically acceptable salts and prodrugs thereof,
wherein the compounds can be in the form of the R- or S-configuration, or a mixture thereof, including a racemic or diastereomeric mixture thereof.

2. A pharmaceutical composition comprising a compound of claim 1, and a pharmaceutically-acceptable carrier or excipient.

3. The composition of claim 2, further comprising one, two, or three additional compounds having anti-HCV activity.

4. A method for treating a host infected with HCV, or for reducing the biological activity of an infection with HCV, comprising administering an effective amount of a compound of claim 1 to a patient in need of treatment thereof.

5. The method of claim 4, wherein the compound of claim 1 is administered in combination with one, two, or three other anti-HCV agent(s).

6. A compound having the formula:

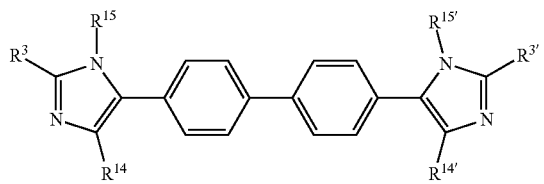

wherein:
R³ is

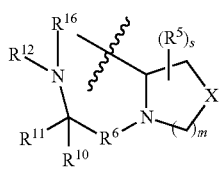

each m is independently 0, 1, or 2;
each s is independently 0, 1, 2, or 3, with the proviso that at least one s is 1;
each X is, independently, O, S, S(O), SO₂, CH₂, CHR⁵, or C(R⁵)₂; provided that when m is 0, X is CH₂, CHR⁵, or C(R⁵)₂;
each R⁵ is independently selected from the group consisting of thioalkyl, thioaryl, SCH₃, SCF₃, sulfoxide alkyl, sulfoxide aryl, S(O)CH₃, S(O)CF₃, sulfone alkyl, sulfone aryl, S(O)₂CH₃, and S(O)₂CF₃ with the proviso that —C(R₅)² can be —C(O),
each R' is, independently, H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, arylalkyl, or if two R' reside on the same nitrogen atom, they can come together to form a $C_{3-6}$ alkyl ring containing none or one heteroatom independently selected from the group consisting of N, O and S; wherein the R' groups can be substituted with one or more hydroxyalkyl, aminoalkyl, and alkoxyalkyl substituents;
with the proviso that C(R⁵)₂ cannot be C(alkoxy)₂, C(OH)₂, C(alkoxy)(OH), or C(halo)(OH), and with the further proviso that C(R⁵)₂ can also be C(=O),
each R⁶ is, independently, —C(O)—, —C(S)— or —C(NR^z)—;
each R¹⁰ and R¹¹ are independently selected from the group consisting of H, alkylcarboxy amino, alkoxyalkyl, alkoxycarbonyl, alkoxycarbonylalkyl, alkyl, alkylcarbonyl, alkylcarbonylalkyl, alkylamino, alkylguanasyl, alkylaryl, aryl, arylalkenyl, arylalkoxy, arylalkyl, aryloxyalkyl, cycloalkyl, cycloakylamino, (cycloalkyl)alkenyl, (cycloalkyl)alkyl, cycloalkyloxyalkyl, haloalkyl, alkylheterocyclyl, heterocyclyl, heterocyclylalkenyl, heterocyclylalkoxy, heterocyclylalkyl, heterocyclyloxyalkyl, and hydroxyalkyl, wherein the groups can be substituted with one or more hydroxyaryl, aminoalkyl, and alkoxyalkyl substituents;
each R¹² and R¹⁶ are, independently, hydrogen, R¹³—C(O)—, R¹³—C(S)—, or R'; each R' is as defined above;
each R¹³ is independently selected from the group consisting of alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, and —N(R')₂, wherein each R' is as defined above;
R¹⁴ and R¹⁴' are, independently, H, halogen, CF₃, hydroxy, $C_{1-6}$ alkoxy, aryl, 5-membered heteroaryl, $C_{1-6}$ alkyl or halo substituted aryl, aryl or halo substituted 5-membered heteroaryl, cyano, $C_{2-6}$ alkynyl, $C_{3-6}$ alkoxyalkyl, alkoxycarbonylalkyl, heterocyclylalkyl, or hydroxyalkyl;
R¹⁵ and R¹⁵' are, independently, hydrogen, $C_{2-6}$ alkoxy, $C_{3-6}$ alkoxyalkyl, alkoxycarbonyl, carbonylalkyl, carbonyl aryl, $C_{1-6}$ alkyl, heterocyclylalkyl, or $C_{2-6}$ hydroxyalkyl,
and pharmaceutically acceptable salts and prodrugs thereof,
wherein the compounds can be in the form of the R- or S-configuration, or a mixture thereof, including a racemic or diastereomeric mixture thereof.

7. The compound of claim 6, wherein R¹⁴ and R¹⁴' are, independently, H or halogen.

8. A composition comprising a compound of claim 6, or a pharmaceutically acceptable salt or prodrug thereof, and a pharmaceutically acceptable carrier.

9. The composition of claim 8, further comprising one, two, or three additional compounds having anti-HCV activity.

10. A method for treating a host infected with HCV or for reducing the biological activity of an infection with HCV comprising administering an effective amount of a compound of claim 6 to a patient in need of treatment thereof.

* * * * *